(12) United States Patent
Ofer

(10) Patent No.: US 12,223,105 B2
(45) Date of Patent: *Feb. 11, 2025

(54) METHODS AND SYSTEMS FOR CONTROLLING AND INTERACTING WITH OBJECTS BASED ON NON-SENSORY INFORMATION RENDERING

(71) Applicant: Moshe Ofer, Ramat Hasharon (IL)

(72) Inventor: Moshe Ofer, Ramat Hasharon (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/134,081

(22) Filed: Apr. 13, 2023

(65) Prior Publication Data

US 2023/0251713 A1 Aug. 10, 2023

Related U.S. Application Data

(63) Continuation-in-part of application No. 17/863,480, filed on Jul. 13, 2022, now Pat. No. 11,733,776.

(60) Provisional application No. 63/226,821, filed on Jul. 29, 2021.

(51) Int. Cl.
*G06F 3/01* (2006.01)
*G05B 15/02* (2006.01)

(52) U.S. Cl.
CPC .............. *G06F 3/015* (2013.01); *G05B 15/02* (2013.01)

(58) Field of Classification Search
CPC ..... G06F 3/015; G05B 15/02; A61B 2503/40; A61B 5/4064
See application file for complete search history.

(56) References Cited

U.S. PATENT DOCUMENTS

| 5,178,161 A * | 1/1993 | Kovacs ................ A61N 1/3605 607/115 |
| 6,175,767 B1 * | 1/2001 | Doyle, Sr. .......... A61N 1/36036 607/57 |
| 6,728,578 B1 | 4/2004 | Voelkel |

(Continued)

FOREIGN PATENT DOCUMENTS

| CN | 103705229 A | 9/2012 |
| CN | 204520668 U | 8/2015 |

(Continued)

OTHER PUBLICATIONS

Pan Wang et al: "Verifying Design through Generative Visualization of Neural Activities", arxiv.org, Cornell University Library, 201 Olin Library Cornell University Ithaca, NY, 14853, Mar. 28, 2021 (Mar. 28, 2021) XP081918295.

(Continued)

*Primary Examiner* — William Lu
(74) *Attorney, Agent, or Firm* — Rivka Friedman

(57) ABSTRACT

A processing subsystem communicates with a region of an animal subject's brain that is responsible for forming concepts without sensory input. The processing subsystem receives brain signals that are representative of a concept formed by the region of the brain without sensory input. The processing subsystem processes the received brain signals to convert the concept to computer readable data that is representative of a tangible form of the concept. The processing subsystem identifies a data record that is associated with one or more data elements of the computer readable data and that is also associated with a real-world object that is related to the concept.

20 Claims, 5 Drawing Sheets

(56) References Cited

U.S. PATENT DOCUMENTS

| | | | |
|---|---|---|---|
| 7,991,475 B1 | 8/2011 | Tang et al. | |
| 8,369,958 B2 | 2/2013 | Kwon et al. | |
| 9,327,120 B2 | 5/2016 | Richter et al. | |
| 9,451,883 B2 | 9/2016 | Gallant et al. | |
| 9,480,582 B2* | 11/2016 | Lundborg | A61F 2/70 |
| 10,123,133 B2* | 11/2018 | Pontoppidan | H04R 25/02 |
| 10,264,990 B2* | 4/2019 | Pasley | A61B 5/6814 |
| 10,441,172 B2* | 10/2019 | Tanaka | A61B 5/0042 |
| 10,925,509 B2* | 2/2021 | Nestor | G06F 18/2431 |
| 11,071,465 B2* | 7/2021 | Angle | A61B 5/24 |
| 11,373,672 B2 | 6/2022 | Mesgarani et al. | |
| 11,395,620 B1* | 7/2022 | Moshe | A61B 5/6868 |
| 11,467,665 B2* | 10/2022 | Gribetz | A61N 1/36082 |
| 11,537,352 B1* | 12/2022 | Clements | G06Q 20/18 |
| 2004/0155112 A1 | 8/2004 | Matsuda | |
| 2004/0172098 A1* | 9/2004 | Greenberg | A61N 1/36046 607/54 |
| 2005/0283202 A1* | 12/2005 | Gellman | A61N 1/3787 607/48 |
| 2008/0161915 A1 | 7/2008 | Ren | |
| 2008/0242950 A1* | 10/2008 | Jung | G16H 40/67 600/300 |
| 2008/0319276 A1* | 12/2008 | Jung | G16H 50/20 600/300 |
| 2009/0125082 A1* | 5/2009 | Schleich | A61N 1/36038 607/57 |
| 2009/0216091 A1 | 8/2009 | Arndt | |
| 2010/0026798 A1* | 2/2010 | Schmid | A61B 5/1113 348/61 |
| 2011/0144471 A1* | 6/2011 | Hsu | B82Y 15/00 29/846 |
| 2011/0227586 A1* | 9/2011 | Lovetri | A61B 5/0507 324/637 |
| 2012/0029302 A1* | 2/2012 | Hsu | G09B 19/00 600/300 |
| 2013/0131535 A1* | 5/2013 | Sun | A61B 5/378 600/544 |
| 2013/0131537 A1 | 5/2013 | Tam | |
| 2013/0184558 A1* | 7/2013 | Gallant | A61B 5/0042 600/409 |
| 2014/0018792 A1* | 1/2014 | Gang | A61B 18/1492 606/41 |
| 2014/0214120 A1* | 7/2014 | Simon | A61N 1/3787 607/46 |
| 2014/0267401 A1 | 9/2014 | Urbach | |
| 2014/0277583 A1* | 9/2014 | Kuntaegowdanahalli | A61F 2/72 623/25 |
| 2015/0119689 A1* | 4/2015 | Pascual-Leone | A61N 2/006 600/407 |
| 2015/0126892 A1* | 5/2015 | Kim | A61B 5/372 600/545 |
| 2015/0142082 A1* | 5/2015 | Simon | A61N 1/36132 607/61 |
| 2015/0248470 A1* | 9/2015 | Coleman | G16H 10/20 707/740 |
| 2016/0073887 A1* | 3/2016 | Lee | H01B 11/22 600/377 |
| 2016/0103487 A1 | 4/2016 | Crawford et al. | |
| 2016/0109851 A1* | 4/2016 | Tsang | G06F 3/011 359/9 |
| 2016/0239084 A1* | 8/2016 | Connor | A61B 5/6803 |
| 2017/0087367 A1* | 3/2017 | Weisend | A61B 5/4064 |
| 2017/0109637 A1* | 4/2017 | Marcu | G06F 11/3696 |
| 2017/0340881 A1* | 11/2017 | Connolly | A61N 1/3606 |
| 2018/0021579 A1* | 1/2018 | Kahana | A61N 1/36082 607/45 |
| 2018/0200389 A1* | 7/2018 | Wong | C09B 23/086 |
| 2018/0245097 A1* | 8/2018 | Vogel | C12Q 1/6897 |
| 2018/0304095 A1* | 10/2018 | Register | A61N 5/0622 |
| 2019/0082990 A1* | 3/2019 | Poltorak | A61B 5/7267 |
| 2019/0227490 A1* | 7/2019 | Waller | G02B 21/06 |
| 2019/0336060 A1* | 11/2019 | Shen | G01B 9/02091 |
| 2019/0357797 A1* | 11/2019 | Nestor | G06V 10/774 |
| 2020/0187841 A1 | 6/2020 | Ayyad | |
| 2020/0196932 A1* | 6/2020 | Johnson | A61B 5/7455 |
| 2021/0293714 A1* | 9/2021 | Matoba | G02B 21/16 |
| 2022/0248148 A1 | 8/2022 | Verhulst et al. | |
| 2022/0417678 A1* | 12/2022 | Moshe | A61B 5/388 |

FOREIGN PATENT DOCUMENTS

| | | | |
|---|---|---|---|
| WO | 2019235458 A1 | 12/2019 | |
| WO | WO-2020242888 A1 * | 12/2020 | |
| WO | WO-2021034138 A1 * | 2/2021 | A61B 5/0022 |

OTHER PUBLICATIONS

Akashi Wataru et al: "Vowel Sound Synthesis from Electroencephalography during Listening and Recalling", Advanced Intelligent Systems, vol. 3, No. 2, Jan. 7, 2021 (Jan. 7, 2021) pp. 2000164, XO055881025, DE ISSN: 2640-4567, DOI: 10.1002/aisy. 202000164.

Niketeghad Soroush et al: "Brain Machine Interfaces for Vision Restoration: The Current State of Cortical Visual Prosthetics", Neurotherapeutics, Springer International Publishing, Cham, vol. 16, No. 1, Sep. 7, 2018 (Sep. 7, 2018), pp. 134-143, XP036880191, ISSN: 1933-7213, DOI: 10.1007/S13311-018-0660-1.

Peter Zu Eulenburg et al: "On the recall of vestibular sensations", Brain Structure and Fuction, Springer, Berlin, DE, vol. 218, No. 1, Feb. 25, 2012 (Feb. 25, 2012), pp. 255-267, XP035156789, ISSN: 1863-2661, DOI: 10.1007/S00429-012-0399-0.

* cited by examiner

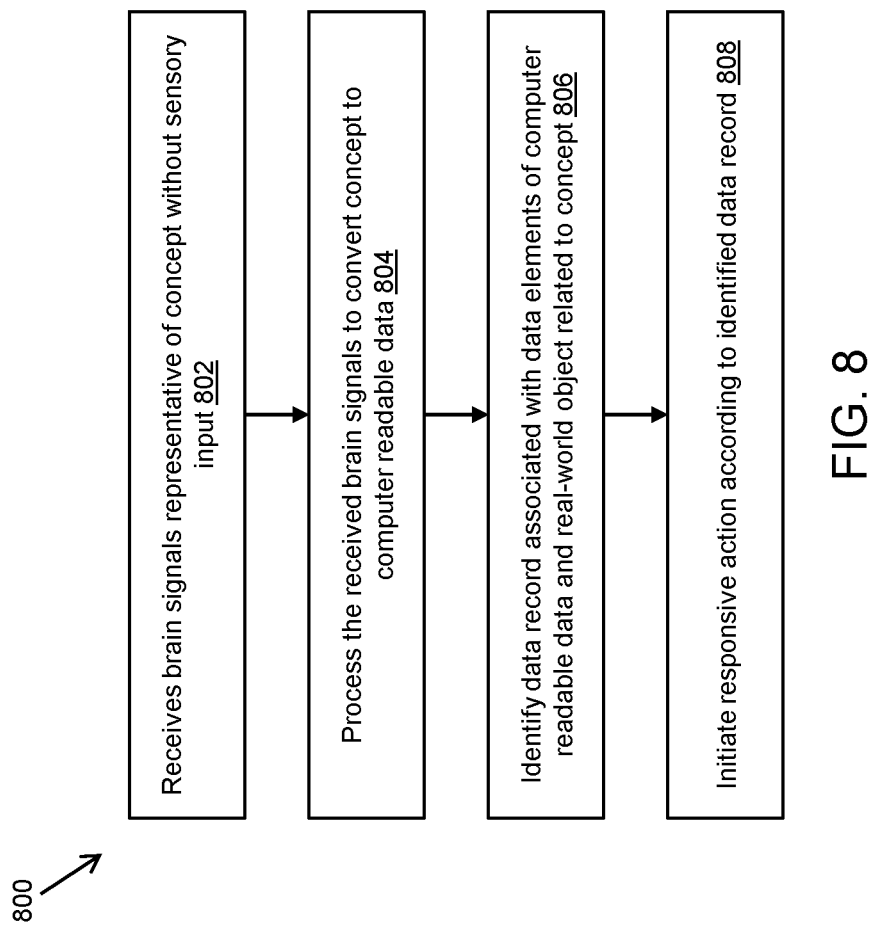

METHODS AND SYSTEMS FOR CONTROLLING AND INTERACTING WITH OBJECTS BASED ON NON-SENSORY INFORMATION RENDERING

CROSS-REFERENCE TO RELATED APPLICATIONS

This application is a continuation-in-part of U.S. patent application Ser. No. 17/863,480, filed Jul. 13, 2022, which claims priority from U.S. Provisional Patent Application No. 63/226,821, filed Jul. 29, 2021, all of the disclosures of which are incorporated by reference in their entireties herein.

TECHNICAL FIELD

The present invention relates to the formation of concepts by the brain, and more particularly methods and systems for rendering and/or injecting such concepts and controlling and/or interacting with real-world objects related to the concepts.

BACKGROUND OF THE INVENTION

Imagination is the ability to form concepts, including objects and sensations, in the mind without any immediate input from the senses. These concepts (objects and sensations) can be in the form of, for example, mental images, phonological passages (i.e., non-acoustic sounds), analogies, and narratives.

SUMMARY OF THE INVENTION

Certain embodiments of the present invention provide a method and system for converting concepts formed in the brain of a subject to computer readable data, and identifying data records associated with the computer readable data in order to, for example, utilize the computer readable data to control and/or interact with real-world objects related to the concepts.

According to the teachings of an embodiment of the present invention, there is provided a method for use with an animal subject having a brain that includes a region that is responsible for forming concepts without sensory input. The method comprises: receiving, by a processing subsystem in communication with the region of the brain, brain signals representative of a concept formed by the region of the brain without sensory input; processing, by the processing subsystem, the received brain signals so as to convert the concept to computer readable data that is representative of a tangible form of the concept; and identifying, by the processing subsystem, a data record associated with one or more data elements of the computer readable data, the data record also associated with a real-world object that is related to the concept.

Optionally, the real-world object is an electronic device.

Optionally, the method further comprises: initiating at least one responsive action according to the identified data record.

Optionally, the at least one responsive action includes activating or controlling the real-world object.

Optionally, the method further comprises: providing feedback to a sensory system of the subject in response to success or failure of initiating the at least one responsive action.

Optionally, the method further comprises: providing feedback to the subject by: i) processing, by the processing subsystem, feedback data indicative of success or failure of initiating the at least one responsive action so as to convert the feedback data into one or more brain signals, and ii) providing the one or more brain signals to the region of the brain such that the success or failure of initiating the at least one responsive action is formed as a concept by the region of the brain without sensory input.

Optionally, the at least one responsive action is selected from a plurality of responsive actions, each responsive action of the plurality of responsive actions being associated with a corresponding data record of a plurality of data records, each data record of the plurality of data records is associated with a corresponding one or more elements of the computer readable data.

Optionally, the real-world object is one of a plurality of real-world objects and the data record is one of a plurality of data records, the plurality of data records is comprised of a plurality of subsets of data records, and each subset is associated with a corresponding real-world object of the plurality of real-world objects.

Optionally, the concept is a mental image or a non-acoustic sound.

Optionally, the computer readable data is image data or audio data.

There is also provided according to an embodiment of the teachings of the present invention a system for use with an animal subject having a brain that includes a region that is responsible for forming concepts without sensory input. The system comprises: a processing subsystem configured for communicating with the region of the brain, the processing subsystem configured to: receive brain signals representative of a concept formed by the region of the brain without sensory input, process the received brain signals so as to convert the concept to computer readable data that is representative of a tangible form of the concept, and identify a data record associated with one or more data elements of the computer readable data, the data record also associated with a real-world object that is related to the concept.

Optionally, the real-world object includes an electronic device.

Optionally, the processing subsystem is further configured to: initiate at least one responsive action according to the identified data record.

Optionally, the at least one responsive action includes activating or controlling the real-world object.

Optionally, the at least one responsive action is selected from a plurality of responsive actions, each responsive action of the plurality of responsive actions being associated with a corresponding data record of a plurality of data records, each data record of the plurality of data records is associated with a corresponding one or more elements of the computer readable data.

Optionally, the real-world object is one of a plurality of real-world objects and the data record is one of a plurality of data records, and the system further comprises: at least one storage medium in communication with the processing subsystem for maintaining the plurality of data records, the plurality of data records is comprised of a plurality of subsets of data records, and each subset is associated with a corresponding real-world object of the plurality of real-world objects.

Optionally, the concept is a mental image or a non-acoustic sound.

Optionally, the computer readable data is image data or audio data.

There is also provided according to an embodiment of the teachings of the present invention a method for use with an animal subject having a brain that includes a region that is responsible for forming concepts without sensory input. The method comprises: receiving, by a processing subsystem in communication with the region of the brain, brain signals representative of a concept formed by the region of the brain without sensory input; processing, by the processing subsystem, the received brain signals so as to convert the concept to computer readable data that is representative of a tangible form of the concept; and activating or controlling a real-world object that is related to the concept and that is associated with one or more data elements of the computer readable data.

Unless otherwise defined herein, all technical and/or scientific terms used herein have the same meaning as commonly understood by one of ordinary skill in the art to which the invention pertains. Although methods and materials similar or equivalent to those described herein may be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the present invention are herein described, by way of example only, with reference to the accompanying drawings. With specific reference to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Attention is now directed to the drawings, where like reference numerals or characters indicate corresponding or like components. In the drawings:

FIG. 8 is a flow diagram illustrating a process for identifying data records to enable control of, or interaction with, objects, according to embodiments of the present invention;

DESCRIPTION OF THE PREFERRED EMBODIMENTS

Figure 2:
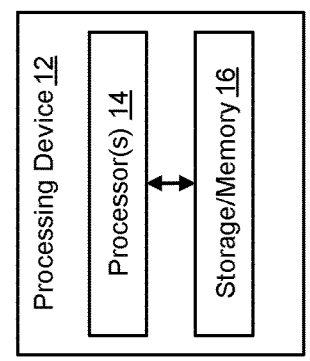
FIG. 2 is a block diagram of an exemplary processing device, according to an embodiment of the present invention.

Embodiments of the present invention provide methods and systems for receiving, by a processing subsystem that is interfaced with a region of an animal subject's brain that is responsible for forming concepts without immediate input from the senses of the subject (i.e., a region that is responsible for imagination), brain signals that are representative of a formed concept or formed concepts, processing (by the processing subsystem) the received brain signals so as to convert the concept or concepts to computer readable data that is representative of a tangible form of the concept or concepts, and identifying (by the processing subsystem) a data record that is associated with one or more data elements of the computer readable data and that is also associated with a real-world object that is related to the concept. The identification of the data record can be used to invoke commands to activate or control the real-world object. This process of receiving brain signals and converting the brain signals to data is referred to interchangeably herein as "imagination rendering", "non-sensory information rendering", or "concept rendering".

In certain embodiments, the processing subsystem is also configured for processing computer readable data, that is representative of a concept or concepts that is or are to be formed by the region of the brain, so as to convert the data into brain signals, and selectively providing the brain signals to the region of the brain such that the concept or concepts that is or are represented by the data is or are formed by the region of the brain without immediate input from the senses of the subject. This process of converting data to brain signals and providing the brain signals to the brain is referred to interchangeably herein as "imagination injection", "imagination inducement", "concept injection", or "concept inducement".

A concept that is formed by the region of the brain without immediate input from the senses that is to be converted to data is referred to interchangeably herein as "a concept that can be rendered", "a render-able concept", "imagination information that can be rendered", "render-able imagination information", "non-sensory information that can be rendered", or "non-sensory render-able information". A concept that is converted to data is referred to interchangeably herein as "rendered imagination information", "rendered non-sensory information", or "a rendered concept".

A concept that is represented by data that is to be converted to brain signals and provided to the region such that the region forms the concept without immediate input from the senses is referred to interchangeably herein as "a concept that can be injected or induced", "an injectable or inducible concept", "imagination information that can be injected or induced", "injectable or inducible imagination information", "non-sensory information that can be injected or induced", or "injectable or inducible non-sensory information". Injectable (or inducible) imagination information may also refer to the data that is representative of an injectable/inducible concept. A concept, represented by data that has been converted to brain signals and provided to the region of the brain such that the concept is formed by the region, is referred to interchangeably herein as "injected or induced imagination information", "an injected or induced concept", or "injected or induced non-sensory information".

As will be discussed in detail below, in certain embodiments the imagination information that can be rendered or injected using the methods and system according to embodiments of the present invention can be visual information (e.g., an image). In other words, in certain embodiments, the concepts can be visual imagination information, also referred to as "imagination images", "imagined images", or "mental images". In other embodiments, the imagination information (i.e., concepts) that can be rendered or injected using the methods and system according to embodiments of the present invention can be audio information (e.g., sound). In other words, in certain embodiments, the concepts can be audio imagination information, also referred to as "sound imagination information", "imagination sounds", "imagined sounds", "non-acoustic sounds", or "mental sounds". In yet further embodiments, the imagination information can be information associated with other senses of the subject, such as touch and smell.

Within the context of this document, in certain cases "imagination" also includes "dreams" and/or "thoughts".

The principles and operation of the methods and systems according to present invention may be better understood with reference to the drawings accompanying the description.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

Figure 1:
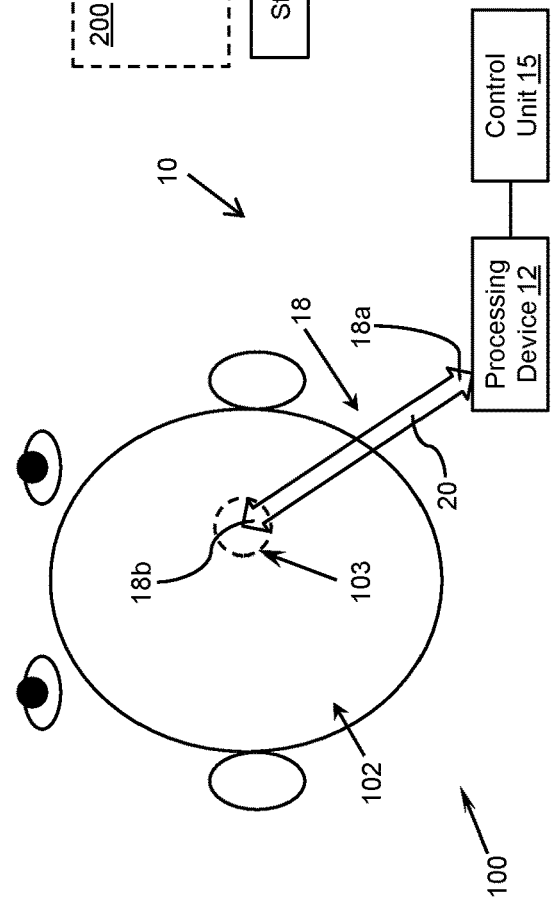
FIG. 1 is a schematic representation of a system having a processing device for interfacing with a brain region that is responsible for forming concepts without immediate input from the senses, and for converting brain signals that are representative of a formed concept or formed concepts to data and vice versa, according to an embodiment of the present invention.

Referring now to the drawings, FIG. 1 is a schematic representation of a system, generally designated 10, according to an embodiment of the present invention, for rendering render-able imagination information and preferably also for injecting injectable imagination information. Generally speaking, the system 10 includes a computerized processing device 12 (referred to hereinafter interchangeably as "processing device") for interfacing (communicatively coupling) with a region 103 of the brain 102 of a subject 100 that is responsible for forming concepts without immediate input from the senses (in particular at least one of vision or hearing) of the subject 100. It is noted that in certain cases one or more concepts may be formed by the region 103 based on input that is derived from immediate input from the senses, for example one or more past or previous immediate input(s) from the senses of the subject 100 or indirect input(s) from the senses of the subject 100. Thus, the region 103 may, in certain cases, form a concept using non-immediate input from the senses of the subject 100, and in other case may form a concept using past immediate input and/or indirect input from the senses of the subject 100. Parenthetically, throughout this document the phrases "without sensory input", "without subject sensory input", and "non-immediate sensory input" are used interchangeably to mean "without immediate input from the senses of the subject". According to certain embodiments, the system 10 is operative to convert render-able imagination information (i.e., render-able concepts) from an intangible form to a tangible form or to computer readable data that is representative of a tangible form of the render-able concept/render-able imagination information. In certain embodiments, the system 10 is operative to convert computer readable data, that is representative of a tangible form of an injectable concept/injectable imagination information, to brain signals that are provided to the subject such that the concept is in intangible form.

In certain non-limiting embodiments, the region 103 of the brain 102 with which the processing device 12 is interfaced is a region that forms visual concepts (i.e., "mental images"). In such embodiments, the imagination information that can be rendered and injected is visual imagination information. In other non-limiting embodiments, the region 103 of the brain 102 with which the processing device 12 is interfaced is a region that is responsible for forming sound concepts (phonological passages) without sensory input (i.e., forming non-acoustic sounds or imagined sounds). In such embodiments, the imagination information that can be rendered and injected is audio/sound imagination information.

It is noted that in the non-limiting illustrative embodiment depicted in FIG. 1 the subject is a human subject. However, the principles of the present invention are applicable to non-human animal subjects as well, including, for example, canine species, feline species, non-human primate species, rodent species, reptile species, bird species, and mammal and non-mammal marine/aquatic species. In general, for a given animal species, the corresponding brain region that is responsible for forming visual concepts or sound concepts can be identified using brain scanning techniques such as magnetic resonance imaging.

In preferred embodiments, the processing device 12 is operative to receive brain signals that are representative of at least one concept formed by the region 103 of the brain without sensory input (i.e., without immediate input from the senses of the subject 100). In other words, the processing device 12 is operative to receive brain signals that carry imagination information (e.g., visual imagination information or sound imagination information) and as such the brain signals are imagination information bearing signals. These brain signals can be any type of information bearing signal that can be read, picked-up, or captured by a computer or a machine or a machine-subject interface. In one particular non-limiting example, the brain signals are in the form of nerve impulses that propagate along a nerve pathway that connects or provides input to the region 103 of the brain 102.

The process of receiving brain signals by the processing device 12 is generally referred to herein as "collecting brain signals" or "collection of brain signals".

The processing device 12 is further operative to process the received brain signals (collected brain signals) so as to generate (produce) data (preferably digital data) from the collected brain signals. In particular, the processing device 12 is operative to process the collected brain signals to convert the render-able imagination information that is carried by the brain signals to data that is representative of a tangible form of the imagination information, thereby rendering the render-able imagination information to tangible form. The data is machine-readable data (i.e., computer readable data). In other words, the data is preferably in a form or format such that the data can be provided to a suitable machine or computer (processor) and read (for further processing or output) by that machine or computer.

In certain embodiments, the received signals that are processed by the processing device 12 can be nerve impulses, or can be representative signals which are produced (i.e., generated) in response to measurement or sampling of brain activity in the region 103 by some type of microdevice, for example a microdevice that has microelectrodes or microtransducers, associated with the processing device 12.

The processing device 12 processes the brain signals (collected brain signals) by applying a mapping function or functions (that contain mapping data) to the brain signals. The mapping function maps between imagination information bearing brain signals and data, i.e., provides a transformation from brain signals to data and vice versa, such that the imagination information (i.e., concept) that is represented by the received brain signals is converted (transformed) to data, thereby rendering render-able imagination information to a tangible form (as a result of the application of the mapping function by the processing device 12). This brain signal to data mapping function is referred to hereinafter interchangeably as an "imagination-data mapping". The imagination-data mapping is preferably a one-to-one mapping. The mapping is preferably such that the data that is converted from the brain signals using the imagination-data mapping function(s) provides a faithful representation of the concept formed by the region 103. In other words, the mapping is preferably such that the data provides a faithful representation of the image or sound that is imagined by the subject 100.

As mentioned, according to certain embodiments, the concept that is formed by the region 103 is a visual concept (i.e., mental image, imagined image), i.e., the processing device 12 converts brain signals that are representative of a mental image. In such embodiments, in one example, the data that is converted from the brain signals can be image data or pixel data whereby the tangible form is a visible image corresponding to the image/pixel data that is a faithful representation of the mental image, which can be viewed by the subject 100 or another viewer.

In other embodiments, the concept that is formed by the region 103 is a sound concept (i.e., imagined sound, non-acoustic sound), i.e., the processing device 12 converts brain signals representative of an imagined sound. In such embodiments, in one example, the data can be sound data in the form of an audio signal or signals, which can be analog or digital (e.g., bits or bytes representing one or more sounds or tones), whereby the tangible form is an acoustic sound corresponding to the audio signal that is a faithful representation of the imagined sound (non-acoustic sound) that can be audibly heard (i.e., that is audibly perceptible) by the subject 100 or another listener.

With continued reference to FIG. 1, refer also to FIG. 2, which shows an example block diagram of the processing device 12 according to a non-limiting embodiment of the present invention. The processing device 12 includes one or more processors 14 coupled to a computerized storage medium 16, such as a computerized memory or the like. The one or more processors 14 can be implemented as any number of computerized processors, including, but not limited to, microprocessors, microcontrollers, application-specific integrated circuits (ASICs), field programmable gate arrays (FPGAs), digital signal processors (DSPs), field-programmable logic arrays (FPLAs), and the like. The processors can be conventional processors or application specific processors or special purpose processors. Conventional processors, such as microprocessors, can be, for example, processors such as those used in servers, computers, and other computerized devices. For example, the processors may include x86 Processors from AMD and Intel, Xeon® and Pentium® processors from Intel, as well as any combinations thereof. Implementation of the one or more processors 14 as quantum computer processors is also contemplated herein. The aforementioned computerized processors include, or may be in electronic communication with computer readable media, which stores program code or instruction sets that, when executed by the computerized processor, cause the computerized processor to perform actions. Types of computer readable media include, but are not limited to, electronic, optical, magnetic, or other storage or transmission devices capable of providing a computerized processor with computer readable instructions. It is noted that above-mentioned implementations of the one or more processors 14 represent a non-exhaustive list of example implementations. It should be apparent to those of ordinary skill in the art that other implementations of the processing device are contemplated herein, including processors founded in processing technologies not described herein or not yet fully developed, such as biological processors or organic semiconductors in the field of biological computing technologies, may be suitable for implementing any of the processing devices discussed herein.

The storage/memory 16 can be any conventional storage media or an application specific or special purpose storage media for storing data or information, which although shown as a single component for representative purposes, may be multiple components. The storage/memory 16 can be implemented in various ways, including, for example, one or more volatile or non-volatile memory, a flash memory, a read-only memory, a random-access memory, and the like, or any combination thereof. In certain embodiments, the storage/memory 16 can include one or more components for storing and maintaining the imagination-data mapping, and at least one component configured to store machine executable instructions that can be executed by the one or more processors 16.

In certain embodiments, the processing device 12 is further operative to perform at least one operation on the generated data (generated by processing brain signals via application of the imagination-data mapping) in accordance with one or more rules or handling criteria. For example, the processing device 12 can be configured to operate on the generated data according to a set of data storage rules or criteria, such that the processing device 12 sends some or all of data representative of the tangible form of the at least one concept to one or more computerized storage/memory devices associated with the processing device 12. Such associated storage/memory devices can include, for example, the storage/memory 16 of the processing device 12

(FIG. 3), or other storage/memory devices that are linked or connected to the processing device 12 as will now be discussed.

Figure 3:
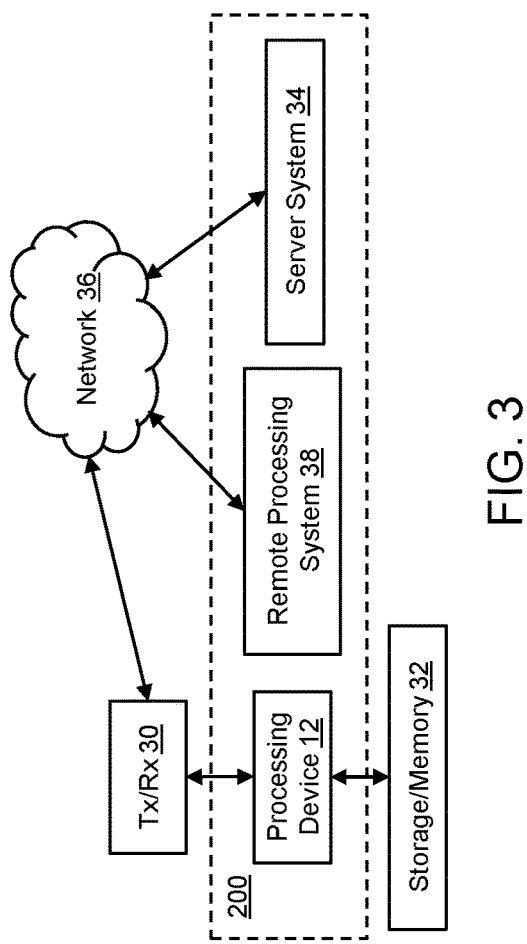
FIG. 3 is a schematic representation of a system environment in which the processing device according to embodiments of the invention can operate, showing a memory for storing data received from the processing device, and a transceiver unit connected to the processing device for exchanging data with a remote server and a remote processing system via a communication network.

With additional reference to FIG. 3, examples of other storage/memory devices that can be linked or connected to the processing device 12 include, for example, an external storage/memory 32, and a server system 34 (having a memory). In embodiments in which the processing device 12 sends some or all of data representative of the tangible form of the at least one concept to a server system 34, the server system may be a remote server system, whereby the processing device 12 sends the data representative of the tangible form of the at least one concept to the server system 34 via a communication network 36 (which can be one or more communication networks, such as cellular networks, local area networks, the Internet, etc.). In such embodiments, the processing device 12 can be linked to a transceiver (Tx/Rx) unit 30 that provides a communication/network interface for transmitting/receiving data to/from (i.e., exchanging data with) the network 36. Also shown in FIG. 3 is a remote processing system 38 that is linked to the processing device 12 via the network 36.

In another non-limiting example, the processing device 12 can be configured to operate on the generated data according to a set of data modification or manipulation rules or criteria to produce modified data. In general, the modified data can be produced from the generated data by one or more of adding data to the generated data (e.g., appending data to or inserting data in the generated data), deleting data from the generated data (e.g., removing subsets of data from the generated data), or changing data elements of the generated data (e.g., changing data values). In embodiments in which the generated data includes pixel data that corresponds to an image that represents visual imagination information, the processing device 12 can modify the data by changing one or more of the pixels to change the image and/or by combining the pixel data with other pixel data representative of another image, which can be a computer-generated image or an image of a real-world scene captured by an image captured device (e.g., camera). The other pixel data can be provided to the processing device 12 via, for example, an image capture device or a memory linked, connected, or otherwise associated with the processing device 12, e.g., the storage/memory 16, external storage/memory 32, server system 34. In embodiments in which the generated data includes an audio signal or signals that corresponds to sound or sounds that represent(s) audio/sound imagination information, the processing device 12 can modify the generated data by, for example, adding additional sound(s) (either from a sound capture device (e.g., microphone) or from a memory associated with the processing device 12, e.g., the storage/memory 16, external storage/memory 32, server system 34), and/or changing or deleting data elements (e.g., bits) of a digital version of the generated audio signal(s), and/or adjusting audio parameters of the audio signal(s), including, for example, volume, pitch, tones, etc. For example, the processing device 12 can modify the audio signal to increases or decrease the volume associated with the audio signal. As another example, the processing device 12 can modify the audio signal to change one or more frequencies (tones) of the sound. As an additional example, the processing device 12 can modify the generated audio signal by performing noise cancellation or interference reduction signal processing on the generated audio signal.

In certain embodiments, the processing device 12 can also convert the modified data to a new set of one or more brain signals (by applying the imagination-data mapping to the modified data), and then provide those signals to the region 103 of the brain, such that a concept represented by the new set of brain signals is formed by the region 103 without sensory input. In other words, the modified image or sound can then be "imagined" by the subject 100.

The modified data can also be stored in in a memory (e.g., storage/memory 16 and/or external storage/memory 32 and/or server system 34).

In another non-limiting example, the processing device 12 can be configured to operate on the generated data according to a set of output rules or criteria. In embodiments in which the generated data includes pixel data that corresponds to an image that represents visual imagination information, the output rules or criteria can include a set of display rules or criteria. For example, the processing device 12 can be configured to provide the generated data to a display device connected or linked to the processing device 12 such that the display device displays one or more images (or video) represented by the pixel data. The processing device 12 can transmit or send the data to such a display device using any suitable image/video transmission format or standard, or any commonly used standards for data transmission, including any of the formats and standards discussed above. As another example, the processing device 12 can provide the generated data for projection or holographic display.

In embodiments in which the generated data includes an audio signal that corresponds to sound(s) that represents audio/sound imagination information, the output rules or criteria can include a set of playback rules or criteria. For example, the processing device 12 can be configured to provide the generated data (audio signal or signals) in digital form to a digital audio playback device (e.g., MP3, digital stereo, etc.) connected or linked to the processing device 12 such that the audio playback device audibly plays sound represented by the generated data. The processing device 12 can transmit or send the data to such an audio playback device using any suitable audio transmission format or standard, or any commonly used standards for data transmission, including any of the formats and standards discussed above. Alternatively, the processing device 12 can be configured to provide the generated data in analog form to an analog audio playback device.

In certain preferred embodiments, the processing device 12 is operative to process obtained/received data (preferably digital data), that is representative of information corresponding to an injectable concept that is to be formed by the region 103 of the brain without sensory input, so as to convert the data into one or more brain signals. The processing device 12 is further operative to selectively provide or transmit the one or more brain signals to the region 103 such that the injectable concept represented by the obtained/received data is formed as a concept by the region 103 without sensory input. In other words, the processing device 12 can obtain or receive data, for example in form of an image represented by pixel data or an analog or digital audio signal that conveys sound, and convert that data to brain signals, and then provide those brain signals to the region 103 of the brain such that a concept of the image or sound is formed by the region 103, i.e., such that the subject 100 imagines the image or the sound. Thus, the system 10 according to certain aspects of the present invention is operative to convert data, that is representative of a tangible form of an injectable concept/injectable imagination information, to brain signals that are provided to the subject such that the concept is in intangible form. In certain embodiments, the processing device 12 can manipulate (i.e., modify) the received/obtained data prior to converting the data to brain signals. The manipulation/modification of the data can be, for example, according to the set of data modification or manipulation rules or criteria discussed above (or a different set of modification or manipulation rules or criteria).

In certain embodiments, the processing device 12 is configured to transmit the brain signals to the region 103 using nerves or nerve fibers at the input to the region 103. For example, the processing device 12 may provide (transmit) the brain signals by inducing nerve transmission of nerve impulses. For example, the processing device 12 may provide the brain signals by sending the brain signals to a microdevice, for example one or more microelectrodes or microtransducers that induces transmission of nerve impulses corresponding to the brain signals.

The data that is obtained or received by the processing device 12, and that is to be converted to brain signals by the processing device 12, can be of various types and/or be from various sources. For example, the data that is to be converted can be image data or sound data, and can be provided to the processing device 12 from a memory associated with the processing device 12 (e.g., the storage/memory 16, external storage/memory 32, server system 34) or any other data source or storage medium. As another example, image data can be provided to the processing device 12 by an image capture device communicatively coupled to the processing device 12. As yet another example, sound data (e.g., audio signals) can be provided to the processing device 12 by a sound capture device communicatively coupled to the processing device 12. In a further example, the data that is to be converted to brain signals by the processing device 12 can be the data that was generated by the processing device 12 from collected brain signals, or modified data resultant from modification of data that was generated by the processing device 12 from collected brain signals.

The conversion of the received data to brain signals is effectuated by applying the imagination-data mapping discussed above. Since the brain of each subject may form concepts differently, the mapping for each subject may be a subject-specific mapping (i.e., the mapping for one subject may be different from the mapping for another subject). However, regardless of the specificity of a given imagination-data mapping, the mapping is preferably such that the brain signals converted from data using the imagination-data mapping function(s) creates a faithful representation of the true image or sound (represented by the data) in the mind of the subject 100.

Various example methods for generating imagination-data mapping functions will be described in detail in subsequent sections of the present disclosure.

The mapping function or functions can be stored in a memory device associated with the processing device 12, as will be discussed further below. In certain embodiments, the mapping function(s) can be stored as a data item or data structure, for example in the form of a data table that stores mapping parameters and configurations. In other embodiments, the mapping function(s) can be stored as an equation or a set of equations that provide a functional relationship between data and brain signals. In yet further embodiments, the mapping function(s) can be expressed as computer-readable code that executes a mapping algorithm, which can be applied to brain signals and/or received data. The aforementioned formats are exemplary only, and other formats of mapping functions are contemplated herein.

With continued reference to FIG. 1, the communicative coupling (interfacing) of the processing device 12 with the region 103 can be effectuated by a machine-subject interfacing arrangement 18 (referred to hereinafter interchangeably as "interfacing arrangement", "machine-subject interface", "machine-brain interface", or simply "interface") that places the processing device 12 in communication with the region 103 of the brain 102. In certain embodiments, the interface 18 can include two interfacing portions, namely a first interfacing portion 18a and a second interfacing portion 18b. The first interfacing portion 18a, also referred to as electronics interfacing portion 18a, is connected to the processing device 12. The second interfacing portion 18b, also referred to as a subject interfacing portion 18b, can be connected or coupled to the region 103 of the brain 102. The two portions 18a, 18b are interconnected via a linking portion 20 which in certain embodiments can provide a wired connection between the two portions 18a, 18b, and in other embodiments can provide a wireless connection between the two portions 18a, 18b.

Various deployment configurations for achieving communicative coupling of the processing device 12 to the region 103 are contemplated herein, and several non-limiting example deployment configurations will be described in further detail below. Some of the deployment configurations described herein require some type of implantation in the subject 100, which can be accomplished using invasive or semi-invasive techniques. For example, invasive techniques can include implantation by surgically accessing the region 103 through the subject's skull (i.e., surgically opening the skull). Surgeries performed on the brain have become common over the years, and it is asserted that a trained human surgeon and/or a robotic surgeon (such as used by the Neuralink Corporation of San Francisco, USA) can perform the necessary implantation. Before describing several deployment configurations, it is noted that the deployment configurations described herein are exemplary only and represent only a non-exhaustive subset of possible deployment options for the processing device 12. Other deployment options may be possible, as will be apparent to those of skill in the art.

In one example deployment configuration according to certain non-limiting embodiments, the processing device 12 communicates with the region 103 by tapping the region 103, for example by connecting the processing device 12 to a transmission route/path that is an input to the region 103. A nerve, nerve bundle, or nerve path is one example of such a transmission route/path. In such a deployment configuration, the processing device 12 preferably remains external to the brain 102 of the subject 100, and most preferably external to the skull so as to be at least partially visible when viewing the subject's head. When the processing device 12 is external to the subject 100, the subject interfacing portion 18b is implanted at or on the segment of the transmission route (that is an input to the region 103) together with either the entirety of the linking portion 20, or a segment of the linking portion 20 that connects to the subject interfacing portion 18b. If only the segment of the linking portion 20 that connects to the subject interfacing portion 18b is implanted, the remaining segment of the linking portion 20, which connects to the electronics interfacing portion 18a, is external to the subject 100.

In another example deployment configuration, the processing device 12 is deployed external to the subject 100, and the subject interfacing portion 18b is implanted at or on the region 103 together with either the entirety of the linking portion 20 or a segment of the linking portion 20 that connects to the subject interfacing portion 18b. If only the segment of the linking portion 20 that connects to the subject interfacing portion 18b is implanted, the remaining segment of the linking portion 20, which connects to the electronics interfacing portion 18a, is external to the subject 100. Such an example deployment configuration is schematically illustrated in FIG. 1.

In yet another example deployment configuration according to certain non-limiting embodiments, the processing device 12 itself, together with the entirety of the interface 18, can be implanted at or on the region 103. In another example deployment configuration according to non-limiting embodiments, the processing device 12 is implanted at or on a segment of the transmission route (that is an input to the region 103).

Non-invasive deployment configurations are also contemplated herein. For example, the interface 18 can be provided by way of an optical magnetic field sensor arrangement or a non-contact modulation arrangement employing, for example, optic, magnetic, or ultrasound techniques. In such configurations, the interface 18 (and its related components) as well the processing device 12 are completely external to the brain 102. The external interface 18 picks up brain signals at the region 103 via non-contact or non-invasive contact means, and provides those picked up brain signals to the processing device 12.

Figure 4:
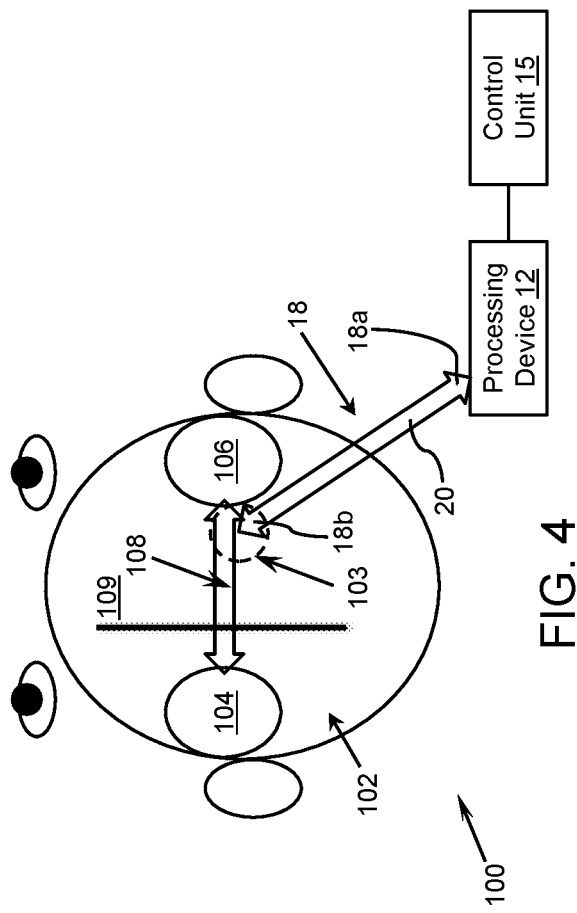
FIG. 4 is a schematic representation of a non-limiting deployment configuration of the processing device in a human brain, showing the processing device coupled to an interface between the occipital lobe and the parieto-occipital sulcus, according to an embodiment of the present invention.

With continued reference to FIGS. 1-3, refer also to FIG. 4 which schematically represents a preferable but not limiting example of the region 103 of the brain with which the processing device 12 is interfaced in embodiments in which the imagination information that can be rendered or injected is visual imagination information. In FIG. 4, various portions of the human brain are schematically illustrated, including the parietal lobe 104, the occipital lobe 106, and the parieto-occipital sulcus (schematically represented as vertical line 109). By way of introduction, the occipital lobe is in the visual processing center of the mammalian brain and contains most of the anatomical region of the visual cortex. The occipital lobe is associated with visuospatial processing, distance and depth perception, color determination, object and facial recognition, and memory formation. Visual information from real events is received at the occipital lobe via the optic nerves and is transmitted from the occipital lobe to the parietal lobe via the parieto-occipital sulcus. Thus, visual real information and visual imagination information (e.g., imagined images) flow between the occipital lobe and parietal lobe in opposite directions. Some discussion of the perception of imagination and reality by the human brain can be found in a Live Science web article published at the following web address: https://www.livescience.com/49244-imagination-reality-brain-flow-direction.html.

Bearing the above in mind, in the non-limiting example embodiment illustrated in FIG. 4 the region 103 is the input to the occipital lobe 106 of the brain 102 from the parieto-occipital sulcus 109. A transmission route, schematically illustrated in FIG. 4 by thick double-headed arrow 108, provides an information interface between the parietal lobe 104 of the brain 102 and the occipital lobe 106. The transmission route (also referred to interchangeably herein as a "transmission path") 108 provides an input to the occipital lobe 106 from the parieto-occipital sulcus 109, and can be, for example, nerve connections formed of one or more nerves or neural fibers. In the illustrated example, the parieto-occipital sulcus 109 represents a boundary between the parietal lobe 104 and the occipital lobe 106, however, the corpus callosum can also provide an interface between the parietal lobe 104 and the occipital lobe 106 instead of, or in addition to, the parieto-occipital sulcus 109, and hence can also be used as the region 103 with which the processing device 12 is interfaced.

In one example deployment configuration of the processing device 12 according to the embodiment illustrated in FIG. 4, the processing device 12 communicates with the region 103 by tapping the interface between the occipital lobe 106 and the parietal lobe 104 and/or the parieto-occipital sulcus 109. For example, the processing device 12 can be connected to the transmission route 108 (e.g., nerves) that links the parietal lobe 104 to the occipital lobe 106. In such a deployment configuration, the subject interfacing portion 18b can be implanted at or on a segment (section, portion) of the transmission route 108 between the occipital lobe 106 and the parieto-occipital sulcus 109, which in certain non-limiting implementations can be effectuated by first cutting the nerves or nerve fibers to produce cut ends of the nerves or nerve fibers, and then connecting the subject interfacing portion 18b to the cut ends. In such a deployment configuration, the processing device 12 preferably remains external to the brain 102 of the subject 100, and most preferably external to the skull so as to be at least partially visible when viewing the subject's head. When the processing device 12 is external to the subject 100, the subject interfacing portion 18b is implanted at or on the segment of the transmission route 108 together with either the entirety of the linking portion 20, or a segment of the linking portion 20 that connects to the subject interfacing portion 18b. If only the segment of the linking portion 20 that connects to the subject interfacing portion 18b is implanted, the remaining segment of the linking portion 20, which connects to the electronics interfacing portion 18a, is external to the subject 100.

Figure 5:
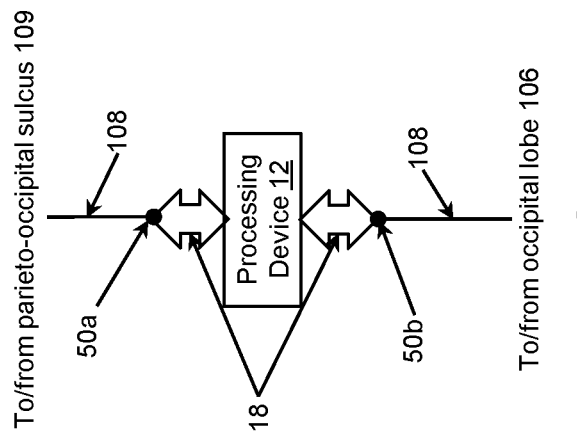
FIG. 5 is a schematic representation of an example deployment configuration of the processing device of FIG. 4 in which the processing device is implanted at a segment of a transmission route between the parietal lobe and the occipital lobe which provides an input to the occipital lobe from the parieto-occipital sulcus, according to an embodiment of the present invention

In another example deployment configuration of the processing device 12 according to the embodiment illustrated in FIG. 4, the processing device 12 is implanted at or on a segment of the transmission route 108. FIG. 5 schematically illustrates such a deployment configuration. Here, the implantation can be effectuated, for example, by first cutting the transmission route 108 (e.g., nerves) to produce cut ends 50a, 50b of the transmission route 108, and then deploying the processing device 12 at the sight of the cut and connecting the cut ends 50a, 50b of the transmission route 108 to the processing device 12 via interface 18.

In embodiments in which the region 103 is the input to the occipital lobe 106 from the parieto-occipital sulcus 109, it is noted that different types of information arriving at the occipital lobe 106 have a common format. Since the information that is input to the occipital lobe 106 have a common format, and since the occipital lobe 106 is in the visual processing center of the brain, in certain embodiments the format of the imagined images (i.e., visual imagination information) arriving from the parietal lobe 104 is of the same format as visual real information. Commonly owned U.S. Pat. No. 11,395,620, which is incorporated by reference in its entirety herein, describes techniques for receiving signals (corresponding to nerve impulses) from the visual cortex (or an equivalent visual processing region of a brain) in response to a subject viewing a scene, and processing those received signals (using a mapping function, referred to as an "impulse-image mapping") to generate image data that is representative of the visual perception of the scene by the subject. U.S. Pat. No. 11,395,620 additionally describes techniques for using the mapping function to process image data that corresponds to an image or images to convert the image data to nerve impulses, and providing those nerve impulses to the visual cortex (or equivalent visual processing region) such that the subject visually perceives the image or images corresponding to the image data. Since in certain embodiments the format of the imagined images (i.e., visual imagination information) arriving from the parietal lobe 104 is a as visual real information, it is a particular feature of certain aspects according to embodiments of the present invention to leverage the mapping methodologies (for converting nerve impulse to image data and vice versa) described in commonly owned U.S. Pat. No. 11,395,620 in order to enable conversion between brain signals/imagination information and image data. In particular, the mapping function(s) described in U.S. Pat. No. 11,395,620 can be used as the imagination-data mapping according to embodiments of the present invention in which the imagination information is visual imagination information (i.e., the concept is a mental image). In other words, in certain embodiments the mapping function(s) described in U.S. Pat. No. 11,395,620 are suitable for converting brain signals that represent a visual concept (i.e., a mental image or an imagined image) to image data, and vice versa.

The following paragraphs describe various methods and techniques for generating the impulse-image mapping, which can be used as the imagination-data mapping in the context of visual imagination information. Further discussion of the impulse-image mapping can be found in U.S. Pat. No. 11,395,620.

According to certain embodiments, generation of the impulse-image mapping (i.e., the imagination-data mapping) can be aided by machine learning (ML) or neural networks (NN) algorithms. For example, the processing device 12 can employ one or more ML or NN algorithms to learn the signal format of nerve impulses (in response to the eyes of the subject viewing a scene or being provided with visual stimuli), and determine the imagination-data mapping by comparing the nerve impulse format to digital images stored in a memory associated with the processing device 12. In certain embodiments, the stored digital images can be generated by an imaging device, such as a camera, associated with the processing device 12.

As part of one non-limiting example process for generating the mapping, a sample picture (i.e., image) can be positioned in front of the eyes of the subject 100 as a visual stimulus such that the light from the sample is collected (captured) by the eyes and the processing device 12 collects the nerve impulses sent from the eyes to the brain 102 (along the optic nerves, which is a nerve or nerves that transmit nerve impulse from the eyes to the visual cortex or equivalent visual processing region of a brain) in response to the subject viewing the sample. A digital image having image data representative of the same sample can also be stored in a memory associated with the processing device 12 (e.g., storage/memory 16). The digital image can be generated, for example, by an imaging device. The resolution of the digital image is preferably in accordance with a standard resolution, such as, for example, 1920 pixels by 1080 pixels, 1280 pixels by 960 pixels, 800 pixels by 600 pixels, etc. Subsequently, a small change can be made to the sample image, for example by changing a single pixel of the sample image, to produce a new sample image. The new sample image is then placed in front of the eyes of the subject 100, and the processing device 12 collects the nerve impulses sent from the eyes to the brain 102 in response to viewing the new sample image. A digital version of the new sample image, i.e., a digital image having digital image data representative of the new sample, is also preferably stored in the memory (e.g., storage/memory 16) associated with the processing device 12. The digital version of the new sample image can be generated by the processing device 12 applying changes to the pixel in the original digital image. This process can continue by making incrementally larger changes to the sample image (e.g., changing two pixels, then changing five pixels, then changing 10 pixels, etc.). For each changed pixel, the change in the nerve impulse from the eyes (compared to the previous sample) is compared with the change between the new digital image data and the previous digital image data. This process can continue using several different sample images, until each nerve impulse from the eye can be matched in a one-to-one fashion to a corresponding image pixel. This matching between each nerve impulse and a corresponding image pixel constitutes a mapping between nerve impulses and images (i.e., an impulse-image mapping), which can be used as the imagination-data mapping.

In certain embodiments, the mapping function is stored as, or together with, a configuration table that maintains nerve-impulse-to-image and image-to-nerve-impulse conversion parameters. The configuration table includes all of the image attributes/features, including color, intensity, position, and a nerve impulse encoding value. The size of the table may be in accordance with the resolution of the image, such that for each pixel (or group of pixels), the image data of that pixel (or group of pixels) has a corresponding value for color, intensity, position, and nerve impulse code. As previously mentioned, in certain embodiments, the mapping function can be stored as an equation or a set of equations that provide a functional relationship between data and brain signals, while in other embodiments the mapping function(s) can be expressed as computer-readable code that executes a mapping algorithm which can be applied to brain signals and/or received data.

In a preferred but non-limiting implementation of the process for generating the mapping, anchor points or regions of the digital image are processed first. The anchor points include a pixel (or a group of pixels, typically made up of at least four pixels) at each of the four corners of the digital image, as well as a pixel (or group of pixels) at the center of each edge (i.e., top, bottom, left, and right) of the digital image, resulting in eight anchor points. The color and intensity of each of the eight pixels are correlated with the corresponding nerve impulses when the corresponding anchor points in the sample picture (based on the determined position of the anchor points) are viewed by the eye of the subject 100. When groups of pixels are used, the average color and intensity of the pixels in each group is calculated and set as the color and intensity of the pixel group.

The color and intensity values for the pixels are stored in a table, together with the values of the registered corresponding nerve impulses. Some or all of the pixel values for the anchor points are then changed, and the sample image displayed to the eye is correspondingly changed, and the color and intensity of each of the eight pixels are correlated with the corresponding nerve impulses when the corresponding anchor points in the sample picture are viewed by the eye. This process can be repeated several times, until the correlation between the pixels of the anchor points (either individual pixels or groups of pixels) and the corresponding nerve impulses is verified. The mapping function generation process can then proceed to changing the color and intensity values of selected pixels or groups of pixels that are non-anchor pixels. The changes can be made according to a particular pre-defined sequence, which can include the sequence of color and intensity values for the selected pixels, and then the sequence of selected pixels. In this way, a pixel or group of pixels is selected (according to a pixel selection sequence), and the color and intensity values of the selected pixel(s) are changed according to a color/intensity sequence, and then another pixel or group of pixels is selected (according to the pixel selection sequence) and the color and intensity values of the selected pixel(s) are changed according to the color/intensity sequence, and so on and so forth, until all combinations of color/intensity values across all pixels have been implemented and the corresponding nerve impulses have been recorded/stored (in the table).

Parenthetically, after each pixel or group of pixels is selected and the color/intensity values have been incrementally changed to produce a correlation between nerve impulses and the color/intensity values for those pixels, the accuracy of the correlation can optionally be checked by converting nerve impulses to digital image data using the partial table having the color/intensity values for the selected pixels.

The full table can then be used to convert nerve impulses (collected in response to the eye viewing a sample picture) to a digital image to produce a generated digital image. The generated digital image is then compared to a digital image stored in the memory (e.g., storage/memory 16) associated with the processing device 12 (which in certain embodiments can be generated by an imaging device camera in response to capturing an image of the sample picture). The comparison can be performed on a pixel-by-pixel basis. If the comparison yields a pixel matching that is within a preferred accuracy level (e.g., if 90% of the pixels of two images are the same), the mapping process is complete. If the comparison does not yield a pixel matching that is within the preferred accuracy level, the correlation process can be repeated, i.e., anchor points can be selected and the color/intensity values of the pixels can be incrementally changed.

The following paragraphs describe another non-limiting example method for generating an imagination-data mapping function in the context of visual imagination information. It is prefaced by saying that this method is particularly suitable for generating a mapping function that is to be used with human subjects. However, this method or a similar method may also be suitable to generate mapping functions that are to be used with other animal species, particularly intelligent animal species such as canines and primates.

Bearing this in mind, a sample image that is easily remembered (i.e., can be easily conjured in the subject's mind) is placed in front of the eyes of a subject whose brain is interfaced with the processing device 12. The sample image is preferably composed of distinct and/or easily distinguishable colors, preferably initially black and white. The sample image can be, for example, thick vertical lines with distinct spaces between the lines.

In a next step, the subject can be asked to close their eyes and recall the sample image (e.g., the black and white vertical lines) from memory or using imagination. First data corresponding to the brain signals collected by the processing device 12 in response to the subject imagining the sample image is captured. Subsequently, a change can be made to the sample image to produce a new sample image. The change is preferably a geometric change, for example, a change to the length or thickness of the vertical lines, or a tilting of the lines such that the lines are no longer vertical but slightly angled. As another example, the change can be a shape change, for example changing thick vertical lines to circles. The geometric/shape change is preferably such that the new sample image is easily distinguishable from the sample image, and can be easily remembered/imagined by the subject without confusing the new sample image with the sample image.

The changes/differences between the sample image and the new sample image can be identified/marked/logged. The new sample image can be viewed by the subject, and then the subject can be asked to recall the new sample image from memory/imagination. Second data corresponding to the brain signals collected by the processing device 12 in response to the subject imagining the new sample image is captured and compared with the first data corresponding to the sample image. The changes in the first and second data can be correlated with the changes between the sample image and the new sample image.

This process of changing the sample image and comparing changes in brain signal data can continue, until each component of the data (produced in response to the subject imagining the image) is mapped or associated with a pixel of the image.

The above-described process can also be repeated by applying a change to the colors of image. For example, if the initial sample image is a black and white image, the process can be repeated by changing the black and white image to a blue and green image, and then a red and yellow image, and so on.

As mentioned above, the above-described example methods for generating mapping functions are suitable in embodiments in which the region 103 is a part of the brain that is responsible for forming visual concepts (i.e., mental images) without sensory input, in particular where the region 103 is the input to the occipital lobe 106 from the parieto-occipital sulcus 109. In embodiments in which the region 103 is a part of the brain that is responsible for forming sound concepts (i.e., the imagination information that can be rendered or injected is sound/audio imagination information), the region 103 can include a segment along one or more of nerves which carry sound-related nerve impulses from the ears to the portion of the brain that performs auditory processing (which in humans and other species including, but not limited to, canine species, feline species, non-human primate species, and rodent species is commonly referred to as the auditory cortex). Commonly owned U.S. patent application Ser. No. 17/728,013, which is incorporated by reference in its entirety herein, describes techniques for receiving signals (corresponding to nerve impulses) from the auditory cortex (or an equivalent audial processing region of a brain) in response to a subject hearing acoustic sounds (i.e., in response to the subject's ears being provided with auditory stimuli), and processing those received signals (using a mapping function, referred to as an "impulse-sound mapping") to generate an audio signal that is representative of the audial perception of the sound heard by the subject. U.S. patent application Ser. No. 17/728,013 additionally describes techniques for using the mapping function to process audio signals that correspond to a sound or sounds to convert the audio signal to nerve impulses, and providing those nerve impulses to the auditory cortex (or equivalent auditory processing region of the brain) such that the subject audially perceives the sound or sounds corresponding to the audio signal. It is therefore a particular feature of certain aspects according to embodiments of the present invention to leverage the mapping methodologies (for converting nerve impulse to audio signals and vice versa) described in commonly owned U.S. patent application Ser. No. 17/728,013 in order to enable conversion between brain signals/imagination information and audio signals/data. In particular, the mapping function(s) described in U.S. patent application Ser. No. 17/728,013 can be used as the imagination-data mapping according to embodiments of the present invention in which the imagination information is audio/sound imagination information (i.e., the concept is a non-acoustic sound). In other words, in certain embodiments the mapping function(s) described in U.S. patent application Ser. No. 17/728,013 are suitable for converting brain signals that represent a sound concept (i.e., a non-acoustic sound or an imagined sound) to an audio signal or signals, and vice versa.

The following paragraphs describe various methods and techniques for generating the impulse-sound mapping, which can be used as the imagination-data mapping in the context of audio/sound imagination information. Further discussion of the impulse-image mapping can be found in U.S. patent application Ser. No. 17/728,013.

According to certain embodiments, the processing device 12 can generate the impulse-sound mapping (i.e., the imagination-data mapping) by employing one or more ML or NN algorithms to learn the signal format of nerve impulses (in response to auditory stimulation of the ears), and then determining the imagination-data mapping by comparing the nerve impulse format to audio signals, including, for example, digital data stored in a memory associated with the processing device 12 and/or analog audio signals generated by a sound capture device (e.g., microphone) in response to capturing sound.

As part of one non-limiting example process for generating the mapping, an audio sample signal can be generated, which is an amplitude varying signal over some fixed time duration. The audio sample signal is an analog signal that may consist of multiple frequency components corresponding to various sounds (frequency tones), which can be isolated using frequency analysis techniques, e.g., Fourier analysis, including Fast Fourier Transform (FFT). Sound vibrations from the audio sample signal are captured by the ears of the subject 100 and the processing device 12 collects the nerve impulses sent from the ears to the auditory region of the brain 102 (along the acoustic nerves) in response to hearing the sample audio.

Parenthetically, the "acoustic nerve" refers herein to any nerve or nerve segment that can transmit pulses (i.e., nerve impulses), converted from mechanical waves (for example vibrations) detected by the ear or ears, to the brain 102 (in particular the auditory region of the brain, e.g., the auditory cortex) so as to be interpreted and perceived by the brain (and hence by the subject) as sound.

Subsequently, the same audio sample can be played such that the sample is captured by a sound capture device connected to the processing device 12. The processing device 12 collects the audio signals transmitted from the sound capture device to the processing device 12, and analyzes/processes the audio sample signal. The analysis/processing can include, for example, digitization (sampling and quantization) and/or frequency analysis (e.g., FFT). Subsequently, a small change to one or more of the signal characteristics can be made to the audio sample signal, for example by changing one or more of the frequency components or an amplitude value of the audio sample signal, to produce a new audio sample signal. The sound vibration from the new audio sample signal is captured by the ears, and the processing device 12 collects the nerve impulses sent from the ears to the auditory region of the brain 102 (along the acoustic nerves) in response to hearing the new audio sample signal. The same new audio sample signal can then be played such that the sample is captured by the sound capture device, and the processing device 12 collects the audio signals transmitted from the sound capture device to the processing device 12. The processing device 12 analyzes/processes the new audio sample signal (e.g., via digitization and/or FFT). This process can continue by changing the characteristics of the audio sample signal either individually one at a time (e.g., changing a single frequency component, or changing an instantaneous amplitude value), or in incrementally larger groups of signal characteristics (e.g., changing multiple frequency components and/or changing multiple instantaneous amplitude values). For each change to the audio sample signal, the change in the nerve impulse from the ears (compared to the previous sample) is compared with the change in the audio signals collected by the processing device 12 from the sound capture device. This process can continue until each nerve impulse from the ear can be matched to a corresponding audio signal component (e.g., sound) transmitted by the sound capture device. This matching between each nerve impulse and a corresponding audio signal component constitutes a mapping between nerve impulses and sounds (i.e., an impulse-sound mapping), which can be used as the imagination-data mapping. Note that the changes to the audio sample signal should preferably cover multiple combinations of sounds (frequency tones), more preferably sounds over any given range of amplitudes and/or frequencies.

It is noted herein that the processing device 12 can employ various techniques for obtaining brain signals (for example, nerve impulses or bio-electrical signals) from the region 103 of the brain 102 and for providing brain signals (converted from data) to the region 103. Such techniques may typically rely on employing microdevices, such as microelectrodes or microtransducers, for measuring (receiving) brain signals, and/or for inducing transmission of brain signals along a segment of a transmission route (e.g., a nerve path) that is an input to the region 103 (e.g., the transmission route 108 of FIG. 5).

In certain embodiments, the brain signals include, or are in the form of, nerve impulses, whereby inducement of transmission includes inducing transmission of nerve impulses along nerve paths or segments of nerves, for example nerves that form the transmission route 108.

Various entities have conducted research, development, and experimentation on connection and interfacing of computer processing devices to the brain, tissue, and nerves via implantation or other invasive or semi-invasive means. One example of such research can be found in a publication by the University of Luxembourg in 2019 entitled "CONNECT—Developing nervous system-on-a-chip" (available at https://wwwfr.uni.lu/lcsb/research/developmental_and_cellular_biology/news/connect_developing_nervous_system_on_a_chip), which describes culturing individual nervous system components and connecting the components in a microfluid chip (integrated circuit).

Examples of research and experimentation in the field of brain-machine interfacing is described in an article published in Procedia Computer Science in 2011, entitled "Brain-Chip Interfaces: The Present and The Future" by Stefano Vassanelli at the NeuroChip Laboratory of the University of Padova in Italy. In one example, computerized processing devices are interfaced to neurons with metal microelectrodes or oxide-insulated electrical microtransducers (e.g., electrolyte-oxide-semiconductor field-effect transistors (EOSFETs) or Electrolyte-Oxide-Semiconductor-Capacitors (EOSCs)) to record (i.e., measure) or stimulate neuron electrical activity. In another example, large-scale high-resolution recordings (i.e., measurements) from individual neurons are obtained using a processing device that either employs or is coupled to a microchip featuring a large Multi-Transistor-Array (MTA). In yet a further example, a microchip featuring a large MTA is used to interface with the cells in vitro by deploying the MTA in contact with brain tissue, where the signals corresponding to nerve impulses are, in one example, in the form of local-field-potentials (LFPs).

An example of a brain-machine interface device is the Neuralink device, developed by Neuralink Corporation of San Francisco, USA. The Neuralink device includes an ASIC that digitizes information obtained from neurons via microelectrodes.

Bearing the above in mind, the following paragraphs provide a high-level description of various non-limiting implementations of the interface 18 that can be used for connecting/interfacing the processing device 12 with the subject 100 so as to provide a machine-subject interface, according to non-limiting example embodiments of the present invention.

Figure 6:
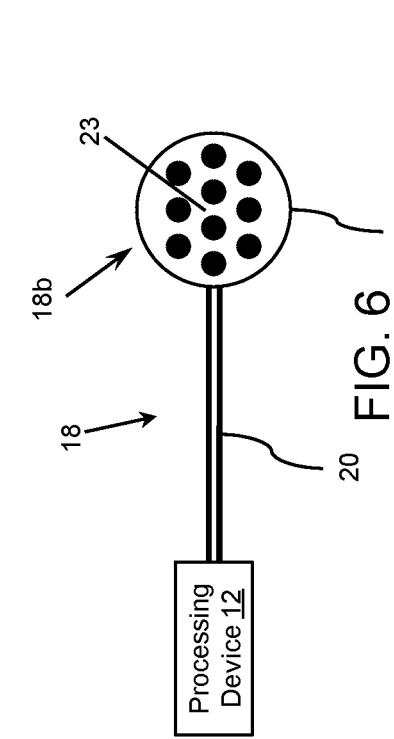
FIG. 6 is a schematic representation of an exemplary wired interface that includes an electrode array that can be used for interfacing between the processing device and the brain region, according to an embodiment of the present invention.

With continued reference to FIGS. 1-5, refer also to FIG. 6, which illustrates a schematic representation of the interface 18 according to a non-limiting embodiment of the invention. Here, the subject interfacing portion 18b includes an electrode array 22, having a plurality of electrodes 23, that is deployed at or on the region 103 (which can, in certain cases coincide with the optic nerves or acoustic nerves). The electrodes 23 are preferably microelectrodes, such as EOSFETs or EOSCs. In embodiments in which the processing device 12 is operative to convert brain signals to data, the electrode array 22 is operative to measure brain signals that are transmitted to the region 103 and produce (in response to the measurements) electrical signals associated with (and representative of) the brain signals, and provide those signals to the processing device 12 in order to enable the processing device 12 to collect the brain signals and process the electrical signals using the imagination-data mapping. In the illustrated embodiment, the linking portion 20 can be implemented as a wire or cable that provides a physical transmission medium along which the electrical signal can propagate to the processing device 12. In certain embodiments, the interface 18 can employ a transducer (preferably a microtransducer as discussed above) as part of the subject interfacing portion 18b, either instead of or in addition to electrode array 22. The transducer can be used together with the processing device 12 for conversion of brain signals to data. For example, the transducer can generate electrical signals in response to receiving (measuring) brain signal activity transmitted to the region 103. The generated electrical signals correspond to (i.e., are representative of) the brain signals (and hence are representative of the concept formed by the brain), and are provided to the processing device 12 for processing using the imagination-data mapping.

In embodiments in which the processing device 12 is operative to convert the data (representative of a concept) to brain signals, and to provide/transmit the brain signals to the region 103 of the brain 102 such that the brain signals are interpreted by the brain 102 and the concept (image or sound) represented by the data is formed by the region 103, the transmission of the brain signals may be effectuated by stimulation of the region 103 (for example stimulation of one or more neurons of the nerves) by a microdevice, e.g., the electrode array 22 (or a transducer). Generally speaking, in such embodiments the processing device 12 can convert (using the imagination-data mapping) data to brain signals (or electrical signals that represent brain signal activity) that are to be transmitted by the region 103. The processing device 12 then provides the brain signals to the region 103 to induce transmission of the brain signals (or provides the electrical impulses to the region 103 to induce transmission of the brain signals represented by electrical impulses). In certain embodiments, the inducing of transmission can be effectuated by the processing device 12 providing electrical signals to the electrode array 22 (or a transducer), which stimulates the neurons at the region 103 in accordance with the electrical signals so as to induce transmission of corresponding nerve impulses.

Figure 7:
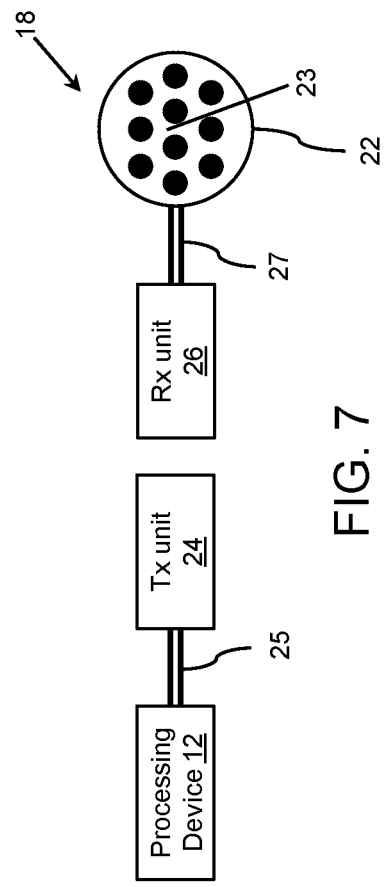
FIG. 7 is a schematic representation of an exemplary wireless interface that can be used for interfacing between the processing device and the brain region, showing a transmitter unit connected to the processing device, and an electrode array connected to a receiver unit, according to an embodiment of the present invention.

FIG. 7 illustrates another embodiment that employs wireless signal transmission for providing electrical signals to the microdevice, represented here as electrode array 22. Here, the processing device 12 is connected to a transmitter (Tx) unit 24 via a wire or cable 25, and the electrode array 22 is connected to a receiver (Rx) unit 26 via a wire or cable 27. The Tx unit 24 includes transmitter circuitry and components for transmitting the electrical signals produced by the processing device 12 via a wireless interface to the Rx unit 26. The Rx unit 26 includes receiver circuitry and components which receive the electrical signals, and provide the received signals to the electrode array 22 which stimulate the region 103 to transmit brain signals corresponding to the electrical signals.

In certain embodiments, the wireless transmission can be RF signal transmission. In such embodiments, the transmitter circuitry and components of the Tx unit 24 can include, for example, signal transmission electronics and components such as one or more antenna, digital-to-analog conversion circuitry, signal modulators, filters, amplifiers, etc., and the receiver circuitry and components of the Rx unit 26 can include, for example, signal reception electronics and components such as one or more antennas, filters, amplifiers, demodulators, etc. In other embodiments, the wireless transmission can be indicative signal transmission whereby the Tx unit 24 and the Rx unit 26 are operative to transmit and receive, respectively, using inductive signal transmission means. In such embodiments, for example, the Tx unit 24 can include inductive coils, and the Rx unit 26 can include an induction receiver.

As mentioned above, in certain embodiments the interface 18 can provide non-contact or non-invasive contact between the processing device 12 and the region of the brain 103. For example, the interface 18 can include, for example, an optical magnetic field sensor arrangement or a non-contact modulation arrangement employing, for example, optic, magnetic, or ultrasound techniques.

In certain embodiments, in particular embodiments in which the processing device 12 is implemented as a biological processor or biological processing element that is cultured or grown in the subject, the interface 18 is the processing device 12 itself.

It is noted that in certain embodiments, the interfacing arrangement 18 can include multiple interfaces. For example, a first interface can be used to effectuate conversion of data to brain signals. The first interface can employ an electrode array 22 or microtransducers (implemented, for example, as EOSCs) connected or linked to the processing device 12 via a wired connection (for example as shown in FIG. 6) or wireless connection (for example as shown in FIG. 7). A second interface can be used to effectuate conversion of brain signals to data. The second interface can employ an electrode array 22 and/or microtransducers (implemented, for example, as EOSFETs) connected or linked to the processing device 12 via a wired connection (for example as shown in FIG. 5). In other embodiments, the second interface can employ non-contact or non-invasive contact means (e.g., an optical magnetic field sensor arrangement or a non-contact modulation arrangement).

As another example, a set of four interfaces can be used. A first interface can be used to effectuate conversion of image data to brain signals (for visual/image imagination injection), and a second interface can be used to effectuate conversion of brain signals to image data (for visual/image imagination rendering). A third interface can be used to effectuate conversion of data (in the form of audio signals) to brain signals (for sound imagination injection), and a fourth interface can be used to effectuate conversion of brain signals to audio signal data (for sound imagination rendering).

Referring now again to FIG. 1, in certain non-limiting embodiments the system 10 also includes a control unit 15 that is connected or linked (electronically) to the processing device 12, and is configured to control the operation of the processing device 12. The control unit 15 preferably includes one or more user input interfaces (e.g., touchscreen, pushbuttons, dials, knobs, electronics keypad, (electronic) keyboard, etc.) that allow the user to provide input to the control unit 15. In response to receiving input via the user input interface, the control unit 15 is preferably operative to provide control commands to the processing device 12 which control or change the operation of the processing device 12.

In one example, the control unit 15 allows the user to define the rules or handling criteria that determine the at least one operation performed on generated data by the processing device 12, as well as to select the handling rule and/or change from the selected rule to another rule. For example, the user can define a set of rules according to which the processing device 12 operates. As an additional example, the user can select an existing rule/set of rules (e.g., data storage rules, data modification rules, output rules) or a newly defined rule/set of rules such that the processing device 12 operates according to the selected rule(s) (e.g., a set of data storage rules (criteria), a set of data modification (manipulation) rules, or a set of output rules (criteria)). In addition, the user can select, via the control unit 15, parameters related to the defined rules. For example, if the user selects that the processing device 12 is to operate according to a set of data modification (manipulation) rules, the user can select how the generated data is to be modified, including selecting any additional images or sounds that are to be used to modify generated data. These additional images or sounds can be received from various sources, including, for example, a computer memory associated with the processing device 12 that stores images or sounds in digital form, an image capture device, an audio capture device or an input device such as a microphone or audio player, and the like.

As another example, if the user selects that the processing device 12 is to operate according to a set of data storage rules, the user can select the memory device (e.g., storage/memory 16, external storage/memory 32, server system 34) for storing data that is representative of the generated data, and may also select which portions (segments or subsamples) of the data are to be stored on which memory device (e.g., the user can select some of the data to be stored locally in storage/memory 16, and select other parts of the data to be stored remotely at server system 34).

The control unit 15 also preferably allows the user to select data that is/are to be converted to brain signals by the processing device 12. The selection can be applied via a menu that is part of the user input interface of the control unit 15. The menu may include a list of images or digital audio tracks or sounds that are stored in a memory associated with the processing device 12. In addition, the control unit 15 preferably allows the user to adjust and set the rate at which brain signals, converted from data by the processing device 12, are provided to the region 103. The rate setting can be applied via the user input interface of the control unit 15.

In certain preferred embodiments, the control unit 15 provides selective switching between different operational modes of the system 10 in response to user input. For example, the control unit 15 can selectively actuate the processing device 12 to retrieve data (images or audio) from a memory (e.g., storage/memory 16, storage/memory 32, a server system 34) or external device (e.g., image capture device or audio capture device). As such, the control unit 15 can enable the user to control if and when data (e.g., image data or audio signals) from a memory (e.g., storage/memory 16, storage/memory 32, a server system 34) or external device are converted to brain signals, and/or if and when such converted brain signals are provided/transmitted to the region 103. In this way, the user can control if and when the subject imagines injected images or sounds.

The control unit 15 is a computerized control unit that includes one or more computer processors coupled to a computerized storage medium (e.g., memory). The one or more processors can be implemented as any number of computerized processors, including, but not limited to, as microprocessors, microcontrollers, ASICs, FPGAs, DSPs, FPLAs, state machines, biological processors, and the like. In microprocessor implementations, the microprocessors can be, for example, conventional processors, such as those used in servers, computers, and other computerized devices. For example, the microprocessors may include x86 Processors from AMD and Intel, Xeon® and Pentium® processors from Intel. The aforementioned computerized processors include, or may be in electronic communication with computer readable media, which stores program code or instruction sets that, when executed by the computerized processor, cause the computerized processor to perform actions. Types of computer readable media include, but are not limited to, electronic, optical, magnetic, or other storage or transmission devices capable of providing a computerized processor with computer readable instructions. The storage/memory of the control unit 15 can be any conventional storage media or any application specific or special purpose storage media and can be implemented in various ways, including, for example, one or more volatile or non-volatile memory, a flash memory, a read-only memory, a random-access memory, and the like, or any combination thereof. In certain embodiments, the storage/memory of the control unit 15 can store machine executable instructions that can be executed by the one or more processors of the control unit 15.

In certain embodiments, the processing device 12 and the control unit 15 share one or more common processors, such that the processing device 12 is operative to perform both processing and control functionality. In other sometimes more preferable embodiments, the control unit 15 and the processing device 12 are separate electronic devices that are electronically connected via a wired or wireless connection. In such embodiments, the control unit 15 can be implemented as a user computer device, which includes, for example, mobile computing devices including but not limited to laptops, smartphones, and tablets, and stationary computing devices including but not limited to desktop computers.

In other embodiments, the control unit 15 is implemented via application software executed on an electronic device, such as a mobile communication device (e.g., smartphone, tablet, etc.) or computer device (e.g., laptop, desktop, etc.).

In embodiments in which the control unit 15 is implemented on a smartphone, tablet, laptop, etc., the software application can provide a user input interface. In certain embodiments, the control unit 15 provides control via direct wired connection or indirect wireless connection to the processing device 12.

In certain embodiments, control functionality of the operation of the processing device 12 and the system 10 is provided algorithmically, for example, by artificial intelligence algorithms executed by the processing device 12, such that the system 10 operates automatically without necessitating any function specific control unit.

Although the embodiments of the present invention described thus far have pertained to a single processing device 12, embodiments employing multiple such processing devices are contemplated herein. For example, a first processing device can be deployed to interface with the input to the occipital lobe 106 from the parieto-occipital sulcus 109 in order to perform for visual imagination rendering and injection, and a second processing device can be deployed to interface with the auditory region of the brain (that performs auditory processing) in order to perform audio/sound imagination rendering and injection.

In addition, although the embodiments of the present invention described thus far have pertained to a processing device 12 that performs brain signal to data conversion and data to brain signal conversion, other embodiments are possible in which the tasks of conversion of brain signals to data and the conversion of data to brain signals are subdivided amongst various processors or processing devices/components. In fact, the processing of brain signals and data as described herein can be performed by any number of processors selected from a plurality of distributed processors which together form a processing subsystem. One or more of the processors can be local to the processing device 12 (and the subject 100) and one or more of the processors can be remote from the processing device 12. Alternatively, only remote processors can be used for processing brain signals and data.

In one example, in the context of the embodiment illustrated in FIGS. 1 and 3, a processing subsystem 200 can include one or more processors of the processing device 12 and one or more processors of the server system 34 or another remote processing system 38 (which can include processing components for processing signals and data) linked to the processing device 12 via the network 36. For example, the processing device 12 can, in certain embodiments, receive brain signals from the region 103 and transmit those signals to the server system 34 (or the remote processing system 38) via the network 36. In such embodiments, the server system 34 (or the remote processing system 38) can process the signals, by applying the imagination-data mapping, to generate data. As another example, the server system 34 (or the remote processing system 38) can modify the generated data. As another example, data (representative of a concept that is to be formed by the region 103 of the brain without sensory input) can be processed by the server system 34 (or the processing system 38), by applying the imagination-data mapping, to convert the data to brain signals. The server system 34 (or the remote processing system 38) can then transmit those signals to the processing device 12, which can then provide the signals to the region of the brain 103.

Thus, generally speaking, the processing subsystem 200 (which by definition includes at least one processor) is configured to perform the tasks of the processing device 12 described above, including one or more of: receiving/obtaining brain signals that are representative of concepts formed by the region 103 of the brain, processing the received/obtained brain signals to convert the concepts to generate data, performing at least one operation on the generated data according to one or more rules, receiving/obtaining data, processing the received/obtained data to convert the received/obtained data to brain signals, and providing the brain signals to the region 103 of the brain.

Although the embodiments of the present invention are of particular use when applied within the context of human imagination and thought, embodiments of the present disclosure may be equally applicable to imagination in non-human animal subjects, including, but not limited to, other primate species (e.g., monkeys, gorillas, etc.), canine species, feline species, reptile species, bird species, marine/aquatic species, etc. In such non-human applications, brain signals can be collected via the same or similar interfacing methods discussed above, and converted to data by the processing device 12 using a species-specific imagination-data mapping. As mentioned above, for a given animal species, the corresponding brain region that is responsible for forming visual or sound concepts can be identified using brain scanning techniques such as magnetic resonance imaging.

Any resultant data can, for example, be output to another system for further processing or use. For example, the images or audio signals generated from brain signals in a canine subject can be provided for display or playback to be seen or heard by a human subject, or can be converted to brain signals using a human imagination-data mapping function and provided to the region 103 of a human subject such that the human subject can imagine the images or sounds as perceived by the canine subject.

According to certain embodiments, the computer readable data, that is generated by the processing subsystem 200 from collected brain signals (e.g., nerve impulses) that are representative of concepts formed by the region 103 without sensory input, can be used to advantage to support interaction with, and/or control of, real-world objects that are related to the concepts. within the context of the present disclosure, the term "real-world object" refers to an object that exists in the real physical world of the subject.

Generally speaking, in such embodiments, the processing subsystem 200 is operative to identify a data record (for example having metadata) that is associated with one or more data elements of the generated computer readable data and that is also associated with a real-world object that is related to the concept that forms the basis from which the computer readable data was generated. The processing subsystem 200 can use the identified data record to invoke commands to activate, control, or otherwise interact with a real-world object that is related to the concept. For example, if the concept is a mental image of a snowflake, the processing subsystem 200 may convert brain signals that represent the snowflake into computer readable image data (including pixel data) that is descriptive of a snowflake. The processing subsystem 200 can then identify a data record (which can, for example, be one of many data records stored in a data record storage such as a database) that is associated with one or more pixels of the snowflake image data, and that is also associated with a real-world object that is related to a concept (i.e., related to the "snowflake"). For example, the real-world object can be a freezer, a refrigerator, an air conditioning unit, or any other object relating to a "cold environment" (i.e., objects "related" to a snowflake). As another example, if the concept is a non-acoustic sound, i.e., an imagined sound, in the form of the word "snowflake", the processing subsystem 200 may convert brain signals that represent the non-acoustic sound into a computer readable audio signal (i.e., audio data such as an MP3 file) that, for example, when played back on an audio playback device (e.g., MP3 player) results in the audio playback device emitting/producing the sound "snowflake". The processing subsystem 200 can then identify a data record that is associated with one or more bytes of the audio signal, for example one or more bytes associated with a portion of the audio signal corresponding to "snow", one or more bytes associated with a portion of the audio signal corresponding to "flake", one or more bytes associated with a portion of the audio signal corresponding to "snowflake", and the like.

The relational data that maintains the relation between real-world objects and concepts can be pre-programmed into a memory associated with the processing subsystem 200 (e.g., storage/memory 32), or can be stored together with the data records in a data record manager. It is noted that the relationship between a concept and a real-world object and/or action can be an intrinsic relationship, or can be an arbitrary relationship that can be assigned by, for example, the user of the system 100.

Figure 9:
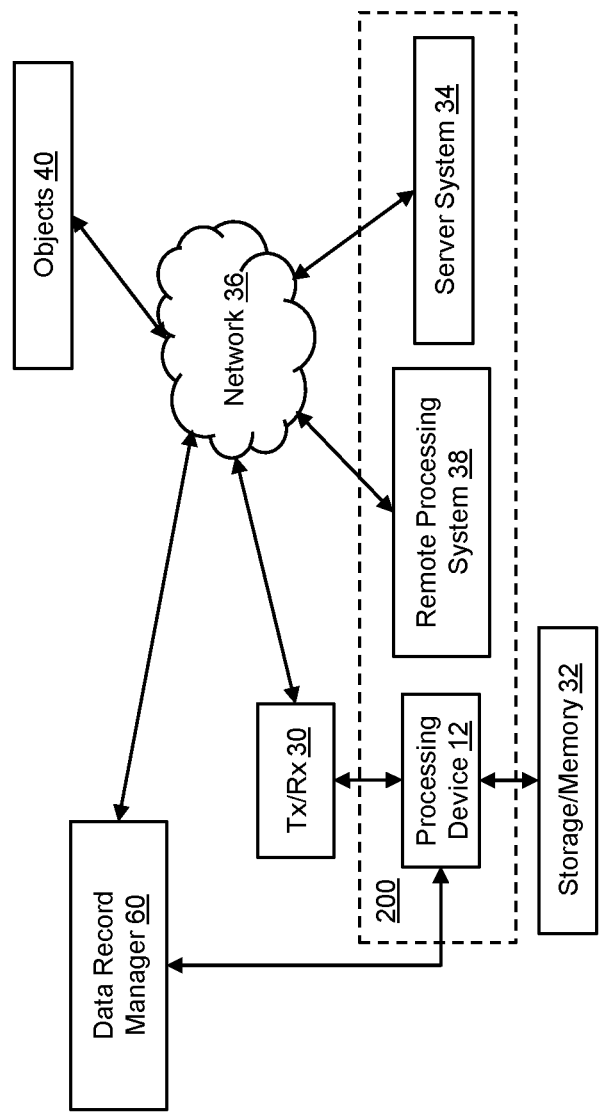
FIG. 9 is a schematic representation of a system environment, similar to FIG. 3, according to another embodiment of the present invention, showing a data record manager and one or more objects that can be interacted with or controlled.
Figure 10:
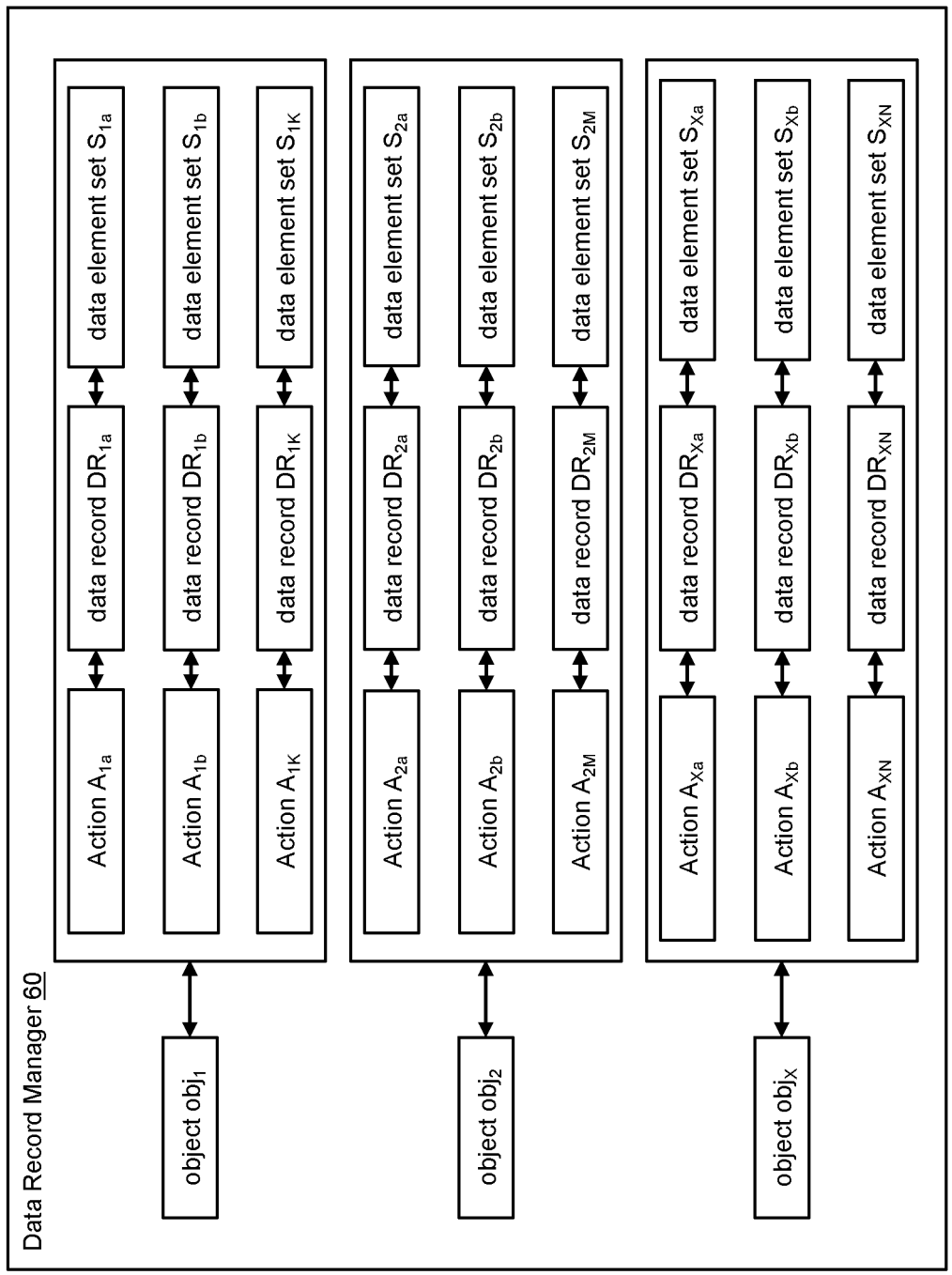
FIG. 10 is a schematic illustration of the data record manager of FIG. 9, showing exemplary data types stored in the data record manager and exemplary relational structure between the stored data types, according to embodiments of the present invention.

With reference to FIGS. 8-10, and with continued reference to FIGS. 1-7, the following paragraphs describe in further detail certain non-limiting embodiments according to the present invention which support interaction with and/or control of real-world objects.

Turning first to FIG. 8, there is shown a flow diagram of a process 800 according to embodiments of the present disclosure. It is appreciated that the process 800 and its sub-processes are performed by the system 10, in particular the processing subsystem 200 and its associated components, such as the processing device 12, the remote processing system 38, and the server system 34. Furthermore, the process 800 and its sub-processes are for example, performed automatically, but can be, for example, performed manually, and are performed, for example, in real time.

The process 800 begins at step 802, in which the processing subsystem 200 receives brain signals that are representative a concept formed by the region 103 without sensory input. At step 804, the processing subsystem 200 processes the received brain signals so as to convert the concept to computer readable data that is representative of a tangible form of the concept. At step 806, the processing subsystem 200 identifies a data record that is associated with one or more data elements of the computer readable data (generated at step 804) and that is also associated with a real-world object that is related (typically intrinsically related) to the concept. At step 808, the processing subsystem 200 initiates a responsive action according to the data record identified at step 806. As will be discussed, the real-world object can, in certain embodiments, be an electronic device (which can include any type of device, machine, or appliance having one or more processor components (including computerized processor components and/or bioprocessor components), and the responsive action typically includes activating, actuating, or controlling the real-world object. The responsive action can, in certain cases, including commanding the real-world object to maintain a current state of operation.

Parenthetically, it is noted that certain, if not many, computer readable data (generated at step 804) may (by design) not be associated with any real-world objects or actions, and therefore in such cases no data record associated with one or more data elements of computer readable data may be identifiable. As should be apparent, if no data record is identifiable, then no action on real-world objects can be invoked by the processing subsystem 200.

The aforementioned data record can be a data object, for example having metadata, that can typically be stored together with other similarly structured data records in a database or data table or other data structure storage. In the non-limiting example illustrated in FIG. 9, a data record manager 60, which can be linked to the processing subsystem 200, can be used to store and maintain the data records. The data record manager 60 can be, for example, a memory, server, database, or any other type of data storage element or medium that can store data records in a structured format. In one non-limiting example, the data record manager 60 can be indirectly linked to the processing device 12 of the processing subsystem 200 via the network 36. In another non-limiting example, the data record manager 60 can be directly linked to the processing device 12 of the processing subsystem 200 through a data bus or other wired data communication interface that supports exchange of data between the processing device 12 and the data record manager 60. Other deployment configurations of the data record manager 60 are also contemplated herein, including, for example, a direct link between the data record manager 60 and the remote processing subsystem 38 and/or the server system 34 through a data bus or other wired data communication interface that supports exchange of data between the data record manager 60 and the remote processing subsystem 38 and/or the server system 34. In certain embodiments, the data record manager 60 can be implemented as part of the remote processing system 38 or the server system 34.

FIG. 10 schematically illustrates the data types stored in the data record manager 60 and the relational structure between the stored data types according to one non-limiting example embodiment. As illustrated, and as will be discussed in detail below, the data types according to the non-limiting example embodiment include: 1) data records (e.g., $DR_{1a}$, $DR_{1b}$, $DR_{2a}$, etc.) that associate between a set of data elements (e.g., group of pixels, etc., see below) and an action and object, 2) data element sets (e.g., $S_{1a}$, $S_{1b}$, $S_{2b}$, etc.) of generate computer readable data that are associated with the data records (the data element sets can be, for example, pixels, groups of pixels, bytes of audio data, and the like), 3) real-world objects (e.g., $obj_1$, $obj_2$, etc.) that are associated with the data records and that are related to concepts from which the computer readable data is formed, and 4) responsive actions (e.g., $A_{1a}$, $A_{1b}$, $A_{2b}$, etc.) that are associated with the data records and that can be applied to the real-world objects.

As illustrated in FIG. 10, a plurality of data records is stored in the data record manager 60. The data records $DR_{1a}$, $DR_{1b}$, . . . $DR_{1K}$ represent a first set of data records stored in the data record manager 60, where K is an integer that represents the number of data records in the first set. Similarly, data records $DR_{2a}$, $DR_{2b}$, . . . $DR_{2M}$ represent a second set of data records stored in the data record manager 60, where M is an integer that represents the number of data records in the second set. Similarly, data records $DR_{Xa}$, $DR_{Xb}$, . . . $DR_{XN}$ represent a last set of data records stored in the data record manager 60, where N is an integer that represents the number of data records in the last set, and X represents the number of sets of data records. As should be apparent, the data records can be partitioned into any suitable number of sets (i.e., X can take on any integer value greater than zero), with each set having any suitable number of data records that can be the same or different from the number of data records in the other sets (i.e., each of K, M, N, etc. can take on any integer value greater than zero).

Each data record is associated with one or more data elements of a generated computer readable data. The one or more data elements that are associated with a particular data record make up a data element set. For example, the data record $DR_{1a}$ is associated with data element set $S_{1a}$, the data record $DR_{1b}$ is associated with data element set $S_{1b}$, and the data record $DR_{1K}$ is associated with data element set $S_{1K}$. Similarly, for example, the data record $DR_{2a}$ is associated with data element set Sea, the data record $DR_{2b}$ is associated with data element set $S_{2b}$, and the data record $DR_{2M}$ is associated with data element set $S_{2M}$. Similarly, for example, the data record $DR_{Xa}$ is associated with data element set $S_{Xa}$, the data record $DR_{Xb}$ is associated with data element set $S_{Xb}$, and the data record $DR_{XN}$ is associated with data element set $S_{XN}$.

The data records of a set are also associated with a real-world object that is related to the concept (i.e., imagined image, sound, etc.). Thus, for example, each of the data records $DR_{1a}$, $DR_{1b}$, . . . $DR_{1K}$ is associated with the object $obj_1$. Similarly, for example, each of the data records $DR_{2a}$, $DR_{2b}$, . . . $DR_{2M}$ is associated with the object $obj_2$, and each of the data records $DR_{Xa}$, $DR_{Xb}$, . . . $DR_{XN}$ is associated with the object $obj_X$.

The data records of a set are also associated with responsive actions that can be invoked such that the associated real-world object performs an action or actions. Thus, for example, the data records $DR_{1a}$, $DR_{1b}$, . . . $DR_{1K}$ are respectively associated with responsive actions $A_{1a}$, $A_{1b}$, . . . $A_{1K}$, which are associated with the object $obj_1$. Similarly, for example, the data records $DR_{2a}$, $DR_{2b}$, . . . $DR_{2M}$ are respectively associated with responsive actions $A_{2a}$, $A_{2b}$, . . . $A_{2M}$, which are associated with the object $obj_2$, and the data records $DR_{Xa}$, $DR_{Xb}$, $DR_{XN}$ are respectively associated with responsive actions $A_{Xa}$, $A_{Xb}$, . . . $A_{XN}$, which are associated with the object $obj_X$.

Thus, according to embodiments of the present invention, there is an association between real-world objects (that are related, for example intrinsically, to a concept) a set of data records, a set of data elements of computer readable data that is generated from the concept, and a set of responsive actions associated with the real-world object. In certain embodiments, the aforementioned associations (or "linkages") are maintained in the data record manager 60, for example as relational data.

Each data record can store various attributes associated with the real-world object with which it is associated. Such attributes can include, for example, functional operative parameters of the object. For example, if the object is an electronic device, the attributes can include activation settings of the electronic device, operational settings and/or actions of the electronic device, and the like. For example, if the object is an air conditioning unit, the attributes stored in the data record (or data records) associated with the air conditioning unit can include, temperature settings, fan settings, timer settings, etc.

It is noted that practically, all of the data elements of a generated computer readable data item should be associated with the same object. Thus, for example, if the data elements of the sets $S_{1a}$, $S_{2b}$, . . . $S_{1K}$ are all elements of the same generated computer readable data item, then all of the data elements in the sets $S_{1a}$, $S_{2b}$, . . . $S_{1K}$ should be associated with the same object (e.g., $obj_1$). For example, if the concept is a mental image of a television remote-control device (i.e., an imagined picture of the remote-control device) such that the computer readable data is image data (which includes pixel data as well as image attributes such as color, intensity, etc.) that is descriptive of the remote-control device, then each data element set of the same image data can correspond to different groups of pixels of the image (i.e., different parts of the image) but is still associated with the same object (e.g., the television controlled by the remote-control device).

In addition, each data element set for a given computer readable data item should correspond (i.e., be associated) with a different responsive action. Moreover, in certain embodiments, the subject can mentally focus on a specific portion of the concept (for example a particular region of the mental image, a particular segment of the non-acoustic sound, etc.). The processing subsystem 200 can process brain signals representative of the focused portion of the concept to generate data elements that are also part of the computer readable data that was generated from the concept. For example, if the concept is a mental image, the subject can mentally focus on a particular region of the mental image such that the processing subsystem 200 generates pixel data associated with that particular region, which is also part of the image data generated from the entire mental image. Thus, for example, if the concept is a mental image of a television remote-control device such that the computer readable data is image data that is descriptive of the remote-control device, each data element set of the same image data can correspond to different pixels of the image (i.e., different parts of the image) and particular pixels can also be generated (or re-generated) when the subject mentally focuses on the part of the mental image corresponding to those particular pixels. Furthermore, each data element set of the same image data can correspond to different pixels of the image (i.e., different parts of the image) and can correspond to (i.e., is associated with) a different responsive action. For example, one part of the image (which can be mentally focused on by the subject) can be volume control which can be associated with a responsive action of actuating or controlling the television (the object associated with the image of the remote-control device) to increase or decrease volume, another part of the image (which can also be mentally focused on) can be channel control which can be associated with a responsive action of actuating or controlling the television associated with the image of the remote-control device to change a channel, and so on. Thus, for example, a data record, say $DR_{1a}$, may be associated with a data element set, say $S_{1a}$, (that corresponds a volume control portion of the generated image of the remote-control device) and may be associated with a first responsive action, say $A_{1a}$, which may include invoking a command to the object, say $obj_1$ (e.g., the television associated with, i.e., controlled by the remote-control device), to adjust the volume of the television, and another data record, say $DR_{1b}$, may be associated with another data element set, say $S_{1b}$, (that corresponds to a channel control portion of the generated image of the remote-control device) and may be associated with a second responsive action, say $A_{1b}$, which may include invoking a command to the same object $obj_1$ (e.g., the television) to change the channel of the television.

It is also noted that different generated computer readable data may be associated with the same object but with different responsive actions. Thus, for example, a data element set, say $S_{1a}$, may be from different one computer readable data and another data element set, say $S_{1b}$, may be from a different computer readable data, but both data element sets $S_{1a}$ and $S_{1b}$ may be associated with the same object, say $obj_1$. As an example, a first concept may be a mental image of a snowflake such that a first computer readable data is image data that is descriptive of a snowflake, and a second concept may be a mental image of a fire such that a second computer readable data is image data that is descriptive of fire. The first image data (snowflake) may correspond to a first data element set, say $S_{1a}$, and the second image data (fire) may correspond to a second data element set, say $S_{1b}$, but both sets of data elements $S_{1a}$ and $S_{1b}$ may be associated with the same object, for example an air conditioning unit, but different responsive actions. Thus, for example, a data record, say $DR_{1a}$, may be associated with the data element set $S_{1a}$ (that corresponds to the generated image of the snowflake) and may be associated with a first responsive action, say A1a, which may include invoking a command to the object $obj_1$ (e.g., air conditioning unit) to lower the output air temperature, and another data record, say $DR_{1b}$, may be associated with the data element set $S_{1b}$ (that corresponds to the generated image of the fire) and may be associated with a second responsive action, say A1b, which may include invoking a command to the object $obj_1$ (e.g., air conditioning unit) to raise the output air temperature.

The specific examples of remote-control device, snowflake, and fire, are an exemplary subset of images only. As should be apparent to those in the art, other images can be produced from a wide range of mental images. For example, for interaction with computers, smartphones, or other computerized electronic devices, mental images such as icons, letters, text strings, and numbers, can be converted to corresponding image data, and can be used to invoke associated responsive actions on associated electronic devices. For example, the subject may visualize as a mental image a string of letters (or one letter at a time in temporal sequence), for example the string of letters 'h' 'e' 'l' 'l' 'o', which can be converted by the processing subsystem 200 to image data that is descriptive of the word "hello". The processing subsystem 200 may then identify a data record, in data record manager 60, that is associated with the image of the word "hello" and can invoke the object associated with the identified data record, which can be, for example, a computer (e.g., laptop, desktop, etc.), to enter the word "hello" in a word processing program or internet browser or any other computer program with textual input, thereby providing a virtual keyboard functionality to the object. It is noted that the processing subsystem 200 can invoke an action with or without identifying meaning of the computer readable data on which it is operating. Continuing with the example of virtual keyboard functionality, the processing subsystem 200 can invoke an object to represent the keying of letters or words that are described by the computer readable data.

Although the above examples discussed above have been described in the context of image data, as noted in previous sections of the disclosure the computer readable data can be of various forms, depending on the type of concept that is being converted, and therefore can include, for example if the concept is a non-acoustic sound (i.e., an imagined sound), an audio signal such as a digital sound file, such as an MP3 or WAV file (or any other digital sound file).

The object for which one or more responsive actions can be initiated can include, for example, electronic devices and any devices having one or more processor components, including, but not limited to, computers (e.g., laptops, desktops, tablets, etc.) and mobile devices (e.g., smartphones, cellular phones, etc.), computer gaming consoles (e.g., PlayStation from Sony Interactive Entertainment LLC of San Mateo, CA, USA, Xbox from Microsoft of Redmond, WA, USA, etc.), printers, scanners, display devices (e.g., televisions, computer monitors (i.e., electronic displays), head-up displays, head-mounted displays, etc.), home appliances (e.g., washing machines, dryers, refrigerators, air conditioning units, ovens, dishwashers, etc.), robotics, remote control units and devices that control other electronic devices (such as displays, appliances, etc.), motor vehicles (e.g., automobiles, motorcycles, electric bicycles, tractors, tractor-trailers, trains, autonomous vehicles, semi-autonomous vehicles, etc.), aircraft, machines having electronic components that include computerized components (such as, for example, medical equipment and medical imaging equipment (e.g., MRI machines, X-ray machines, etc.), assembly lines, production lines, power tools, etc.), and the like.

It is noted that in order to enable control of any object by the system 10 according to embodiments of the present disclosure, such objects should be in electronic or data communication with the system 10 such that communication messages, including command-and-control messages and instructions, can be exchanged between the system 10 and the object(s). In one set of non-limiting examples, the objects are network-enabled devices, and communicate with the system 10 via a communication network, such as the network 36. For example, the objects can be fitted with a network device to become "smart" electronic devices, as is well-known in the art. In other examples, an object, as an electronic device, may be a pre-configured as a network-enabled device, for example pre-configured with wireless network communication hardware such as Bluetooth compliant hardware. For example, FIG. 9 schematically illustrates objects 40 as being part of the networked system environment in which the system 10 can be deployed according to embodiments of the present disclosure. In the non-limiting embodiment illustrated in FIG. 9, the Tx/Rx unit 30 provides a communication/network interface for transmitting/receiving data to/from (i.e., exchanging data with) one or more objects (e.g., network devices) 40 via the network 36. It is noted, however, that other networked communication interfaces are possible.

In certain situations, it may be advantages or beneficial for the subject to receive some type of feedback from the system 10 (in particular the processing subsystem 200) when the system 10 initiates responsive actions. In certain embodiments, the processing subsystem 200 provides feedback to the sensory system or the brain of the subject in response to success or failure of initiating the responsive action. For example, if the processing subsystem 200 initiates an action that includes controlling or activating an object, the processing subsystem 200 can send one feedback to the sensory system of the subject if the action initiated by the processing subsystem is successful, and can send another feedback to the sensory system of the subject if the action initiated by the processing subsystem is unsuccessful. When providing feedback to the sensory system of the subject, the feedback can be in the form of one or more of visual feedback, audio feedback, and touch feedback.

In certain embodiments, the processing subsystem 200 can provide the feedback to the subject as non-sensory feedback via injection of feedback data to the appropriate region of the subject's brain. For example, the processing subsystem 200 may process feedback data, that is indicative of the success or failure of the responsive action, so as to convert the feedback data into one or more brain signals, and may then provide the one or more brain signals to the region 103 of the subject's brain such that the success or failure of the responsive action is formed as a concept by the region of the brain without sensory input. In other embodiments, the processing subsystem 200 can provide the feedback to the subject's sensory system by injection of feedback data to the appropriate region of the subject's brain. For example, the processing subsystem 200 may process sensory feedback data (e.g., visual feedback data, aural feedback data, etc.), that is indicative of the success or failure of the responsive action, so as to convert the feedback data into one or more brain signals, and may then provide the one or more brain signals to the appropriate region of the subject's brain (e.g., visual cortex, audial cortex, etc.) such that the subject visually or aurally perceives the feedback indicating success or failure of the responsive action.

In certain embodiments, the subject can attempt to interact with the object again, based on the feedback received by the subject.

In certain embodiments, the processing subsystem 200 is configured to identify data records based solely on the computer readable data that is generated from the concept. In other embodiments, however, the processing subsystem 200 may be configured to identify data records based on a combination of the generated computer readable data and one or more detected actions or inputs. These detected actions or inputs can include one or more of sensory input (e.g., visual perception, aural perception, touch/feel, smell, etc.) or non-sensory input (e.g., additional mental concepts) which can be different from the type of mental concept upon which the computer readable data generated by the processing subsystem 200 is based. For example, if the computer readable data is image data (i.e., the concept is a mental image), the additional non-sensory input can be computer readable data that was generated from a non-acoustic sound.

In certain embodiments, the processing subsystem 200 is configured to initiate a responsive action to invoke an associated object to perform a command only if the identified data record is associated with a specific one or more data elements of the computer readable data that is pre-programmed into a memory associated with the processing subsystem 200. For example, the processing subsystem 200 may be configured to initiate a command only if the data elements associated with the identified data record is pixel data from a pre-configured image or a pre-determined modification (e.g., color change, shape change, etc.) of an image.

In certain embodiments, the processing subsystem 200 can produce computer readable data from collected brain signals that are generated while the subject performs actions in order to increase the efficacy of the responsive action invocation and the association of objects. For example, if the subject activates an air conditioning unit in order to lower the ambient air temperature in a room, the processing subsystem 200 can be configured to collect brain signals that are representative of a mental concept, such as a mental image of a desert, formed in the region 103 of the brain while the subject performs the air condition activation. The processing subsystem 200 can then generate image data that is representative of the concept (e.g., image data descriptive of a desert). The processing subsystem 200 can then update the data record manager 60 to associate together the object (as an air conditioning unit), the image of the desert, and the responsive action of actuating the object to lower the temperature. As should be apparent, this process of generating computer readable data while the subject performs tasks or actions and updating associations in the data record manager 60 can be repeated as needed. This process can be used to advantage in several situations, for example, non-human animal training scenarios in which the animal can understand the relationship between their mental images and actions performed by objects. For example, a dog can form a mental image of a dog treat, which can invoke a dog treat dispensing machine to dispense a dog treat.

Returning to FIG. 8, it should be appreciated that the step of identifying the data record (step 806) can be performed by the processing subsystem 200 by, for example, searching through the plurality of data records stored/maintained in the data record manager 60, and then marking or flagging the correct data record that is associated with the data element(s) of the computer readable data (generated at step 804). In certain cases, the processing subsystem 200 may perform the searching and marking/flagging by remote processing requests via a network (e.g., network 36), for example if the data record manager 60 and the processing components of the processing subsystem 200 are remote from each other (for example if the processing device 12 and/or the remote processing system 38 and/or the server system 34 are remote from the data record manager 60). The remote processing requests can include, for example, exchanges of network message via the network (e.g., network 36). In other cases, for example where the data record manager 60 is part of the processing subsystem 200 (for example maintained in a memory of the processing device 12 or the remote processing system 38 or the server system 34), the processing subsystem 200 may perform the searching and marking/flagging by local processing requests.

In addition, it should be appreciated that the step of initiating a responsive action (step 808) can be performed by the processing subsystem 200 by, for example, sending communication messages, including command-and-control messages and instructions, that carry responsive action instructions. For example, the processing subsystem 200 can initiate a responsive action by sending a communication message, that carries the responsive action instructions, to the object via a network interface (e.g., Tx/Rx unit 30) over a network (e.g., the network 36).

It is noted that the representation of the data types and the relational structure therebetween illustrated in FIG. 10 is for example purposes only in an effort to illustrate more clearly the relationships between real-objects, actions, and computer readable data generated from concepts. Other data structures relationships are contemplated herein which enable controlling and/or interacting with real-world objects that are related to concepts.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, non-transitory storage media such as a magnetic hard-disk and/or removable media, for storing instructions and/or data. Optionally, a network connection is provided as well. A display and/or a user input device such as a keyboard or mouse are optionally provided as well.

For example, any combination of one or more non-transitory computer readable (storage) medium(s) may be utilized in accordance with the above-listed embodiments of the present invention. A non-transitory computer readable (storage) medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

As will be understood with reference to the paragraphs and the referenced drawings, provided above, various embodiments of computer-implemented methods are provided herein, some of which can be performed by various embodiments of apparatuses and systems described herein and some of which can be performed according to instructions stored in non-transitory computer-readable storage media described herein. Still, some embodiments of computer-implemented methods provided herein can be performed by other apparatuses or systems and can be performed according to instructions stored in computer-readable storage media other than that described herein, as will become apparent to those having skill in the art with reference to the embodiments described herein. Any reference to systems and computer-readable storage media with respect to the following computer-implemented methods is provided for explanatory purposes, and is not intended to limit any of such systems and any of such non-transitory computer-readable storage media with regard to embodiments of computer-implemented methods described above. Likewise, any reference to the following computer-implemented methods with respect to systems and computer-readable storage media is provided for explanatory purposes, and is not intended to limit any of such computer-implemented methods disclosed herein.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

As used herein, the singular form "a", "an" and "the" include plural references unless the context clearly dictates otherwise. For example, reference to a single nerve can also refer to both nerves of a nerve pair. Furthermore, reference to both nerves of a nerve pair can also refer to a single nerve, unless the context clearly dictates otherwise.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The above-described processes including portions thereof can be performed by software, hardware and combinations thereof. These processes and portions thereof can be performed by computers, computer-type devices, workstations, processors, micro-processors, other electronic searching tools and memory and other non-transitory storage-type devices associated therewith. The processes and portions thereof can also be embodied in programmable non-transitory storage media, for example, compact discs (CDs) or other discs including magnetic, optical, etc., readable by a machine or the like, or other computer usable storage media, including magnetic, optical, or semiconductor storage, or other source of electronic signals.

The processes (methods) and systems, including components thereof, herein have been described with exemplary reference to specific hardware and software. The processes (methods) have been described as exemplary, whereby specific steps and their order can be omitted and/or changed by persons of ordinary skill in the art to reduce these embodiments to practice without undue experimentation. The processes (methods) and systems have been described in a manner sufficient to enable persons of ordinary skill in the art to readily adapt other hardware and software as may be needed to reduce any of the embodiments to practice without undue experimentation and using conventional techniques.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

Although the invention has been described in conjunction with specific embodiments thereof, it is evident that many alternatives, modifications, and variations will be apparent to those skilled in the art. Accordingly, it is intended to embrace all such alternatives, modifications and variations that fall within the spirit and broad scope of the appended claims.

What is claimed is:

1. A method for use with an animal subject having a brain that includes a region that is responsible for forming concepts without sensory input, the method comprising:
receiving, by a processing subsystem in communication with the region of the brain, brain signals representative of a concept formed by the region of the brain without sensory input;
processing, by the processing subsystem, the received brain signals so as to convert the concept to computer readable data that is representative of a tangible form of the concept, wherein the processing includes applying to the received brain signals at least one mapping that maps between brain signals and computer readable data, wherein the at least one mapping is a one-to-one mapping such that each brain signal is mapped to a corresponding data element of computer readable data; and
identifying, by the processing subsystem, a data record associated with one or more data elements of the computer readable data, the data record also associated with a real-world object that is related to the concept.

2. The method of claim 1, wherein the real-world object is an electronic device.

3. The method of claim 1, further comprising: initiating at least one responsive action according to the identified data record.

4. The method of claim 3, wherein the at least one responsive action includes activating or controlling the real-world object.

5. The method of claim 3, further comprising: providing feedback to a sensory system of the subject in response to success or failure of initiating the at least one responsive action.

6. The method of claim 3, further comprising: providing feedback to the subject by: i) processing, by the processing subsystem, feedback data indicative of success or failure of initiating the at least one responsive action so as to convert the feedback data into one or more brain signals, and ii) providing the one or more brain signals to the region of the brain such that the success or failure of initiating the at least one responsive action is formed as a concept by the region of the brain without sensory input.

7. The method of claim 1, wherein the at least one responsive action is selected from a plurality of responsive actions, each responsive action of the plurality of responsive actions being associated with a corresponding data record of a plurality of data records, wherein each data record of the plurality of data records is associated with a corresponding one or more elements of the computer readable data.

8. The method of claim 1, wherein the real-world object is one of a plurality of real-world objects and the data record is one of a plurality of data records, wherein the plurality of data records is comprised of a plurality of subsets of data records, and wherein each subset is associated with a corresponding real-world object of the plurality of real-world objects.

9. The method of claim 1, wherein the concept is a mental image or a non-acoustic sound.

10. The method of claim 1, wherein the computer readable data is image data or audio data.

11. A system for use with an animal subject having a brain that includes a region that is responsible for forming concepts without sensory input, the system comprising:
a processing subsystem configured for communicating with the region of the brain, the processing subsystem configured to:
receive brain signals representative of a concept formed by the region of the brain without sensory input,
process the received brain signals so as to convert the concept to computer readable data that is representative of a tangible form of the concept, wherein the processing subsystem is configured to process the received brain signals by applying to the received brain signals at least one mapping that maps between brain signals and computer readable data, wherein the at least one mapping is a one-to-one mapping such that each brain signal is mapped to a corresponding data element of computer readable data, and
identify a data record associated with one or more data elements of the computer readable data, the data record also associated with a real-world object that is related to the concept.

12. The system of claim 11, wherein the real-world object includes an electronic device.

13. The system of claim 11, wherein the processing subsystem is further configured to: initiate at least one responsive action according to the identified data record.

14. The system of claim 13, wherein the at least one responsive action includes activating or controlling the real-world object.

15. The system of claim 1, wherein the at least one responsive action is selected from a plurality of responsive actions, each responsive action of the plurality of responsive actions being associated with a corresponding data record of a plurality of data records, wherein each data record of the plurality of data records is associated with a corresponding one or more elements of the computer readable data.

16. The system of claim 11, wherein the real-world object is one of a plurality of real-world objects and the data record is one of a plurality of data records, the system further comprising: at least one storage medium in communication with the processing subsystem for maintaining the plurality of data records, wherein the plurality of data records is comprised of a plurality of subsets of data records, wherein each subset is associated with a corresponding real-world object of the plurality of real-world objects.

17. The system of claim 11, wherein the concept is a mental image or a non-acoustic sound.

18. The system of claim 11, wherein the computer readable data is image data or audio data.

19. A method for use with an animal subject having a brain that includes a region that is responsible for forming concepts without sensory input, the method comprising:
receiving, by a processing subsystem in communication with the region of the brain, brain signals representative of a concept formed by the region of the brain without sensory input;
processing, by the processing subsystem, the received brain signals so as to convert the concept to computer readable data that is representative of a tangible form of the concept, wherein the processing includes applying to the received brain signals at least one mapping that maps between brain signals and computer readable data, wherein the at least one mapping is a one-to-one mapping such that each brain signal is mapped to a corresponding data element of computer readable data; and activating or controlling a real-world object that is related to the concept and that is associated with one or more data elements of the computer readable data.

20. The method of claim 1, wherein the real-world object includes at least one biological component.

\* \* \* \* \*